US00RE42611E

(19) United States
(12) Reissued Patent
Liscio et al.

(10) Patent Number: US RE42,611 E
(45) Date of Reissued Patent: Aug. 16, 2011

(54) CONTINUOUS BATTERY CHARGER SYSTEM

(75) Inventors: Edward P. Liscio, Murrysville, PA (US); John A. Brosovich, Pittsburgh, PA (US); Richard A. Riggio, Murrysville, PA (US); Mark Trocki, Cheswick, PA (US)

(73) Assignee: Medrad, Inc., Indianola, PA (US)

(21) Appl. No.: 12/116,505

(22) Filed: May 7, 2008

Related U.S. Patent Documents

Reissue of:
(64) Patent No.: 7,224,143
Issued: May 29, 2007
Appl. No.: 10/723,183
Filed: Nov. 26, 2003

U.S. Applications:
(60) Provisional application No. 60/429,511, filed on Nov. 27, 2002.

(51) Int. Cl.
*H01M 10/46* (2006.01)
*H02J 7/00* (2006.01)

(52) U.S. Cl. ..... 320/114; 320/103; 320/111; 320/115; 320/127; 320/128; 429/64; 340/636.1; 604/131; 604/132

(58) Field of Classification Search ..... 320/107, 320/111, 114, 115, 127, 128, 103; 604/131, 604/132; 98/107, 111, 114, 115, 127, 128; 340/636.1; 429/64
See application file for complete search history.

(56) References Cited

U.S. PATENT DOCUMENTS 5,160,879 A * 11/1992 Tortola et al. ..... 320/111
5,494,036 A 2/1996 Uber, III et al.
5,963,015 A * 10/1999 Lee ..... 320/128
2002/0008497 A1 * 1/2002 Tanaka et al. ..... 320/128
2002/0169415 A1 11/2002 Staats et al.

OTHER PUBLICATIONS

Mallinckrodt, Optistar MR Digital Injection System, Service and Parts Manual, Apr. 2001.
Kingbright, 3.5×2.8 MM SMD Chip LED Lamp, Datasheet, pp. 1-4, Dec. 18, 2002.
Condor DC Power Supplies Inc., GLM 65 Series, Datasheet, pp. 1-2, Jul. 30, 2002.
Burr-Brown, INA 1381 INA 168, Datasheet, pp. 1-10, Aug. 2000.
ST Microelectronics, D45H5/D45H8/D45H11, Datasheet, pp. 1-4, Jun. 1998.
Fairchild Semiconductor, LM2903/LM29031, LM393/LM393A, LM293/LM293A, Datasheet, pp. 1-8, Dec. 21, 2001.

(Continued)

*Primary Examiner* — Edward Tso
*Assistant Examiner* — Arun Williams
(74) *Attorney, Agent, or Firm* — James R. Stevenson

(57) ABSTRACT

A battery charger system, for use with an injector system, comprises a power supply and a battery pack. The power supply converts AC power to DC power. The battery pack includes a battery and a charging module. The module monitors the operating mode of the injector system. When the battery pack is disconnected from the injection control unit, the module enables the power supply to charge the battery with DC power. When the battery pack is connected to the injection control unit: (A) upon detecting the injector system in an idle mode, the module routes DC power from the power supply to both the battery for charging thereof and the injection control unit for operation thereof; and (B) upon detecting the injector system in a non-idle mode, the module prevents the power supply from charging the battery and enables the battery to provide DC power to the injection control unit.

30 Claims, 16 Drawing Sheets

OTHER PUBLICATIONS

On Semiconductor, MBRB4030 Datasheet, pp. 1-8, May 2003.
Analog Devices, 5V Precision Voltage Reference/Temperature Transducer, Datasheet, pp. 1-12, Oct. 2002.
Vishay Semiconductors, SS32 Thru SS36, Datasheet, pp. 1-2, Jul. 1 2002.
Unitrobe Products From Texas Instruments, UC2906 UC3906, Datasheet for Sealed Lead-Acid Battery Charger, pp. 1-8, Jul. 2003.
BB Battery Co. Ltd, Maintenance Free Rechargable Sealed Lead-Acid Battery, Datasheet.
Philips Semiconductors, N-Channel Trenchmos Transistor Logic Level FET, Datasheet, pp. 1-4, Aug. 2000.
Condor DC Power Supplies Inc., GLC65 Commercial/GLM65 Medical, Datasheet, pp. 36-37.
Stmicroelectronics. D45H5/D45H8/D45H11, Datasheet, pp. 1-4, Jun. 1998.
Fairchild Semiconductor, LM2903/LM2903I,LM393/LM393A, LM293/LM293A, Datasheet, pp. 1-8, Dec. 21, 2001.
Fairchild Semiconductor, Advanced Power MOSFET SFW/I9Z24 Datasheet.
Unitrode Products From Texas Instruments, UC2906 UC3906, Datasheet for Sealed Lead-Acid Battery Charger, pp. 1-8, Jul. 2003.

* cited by examiner

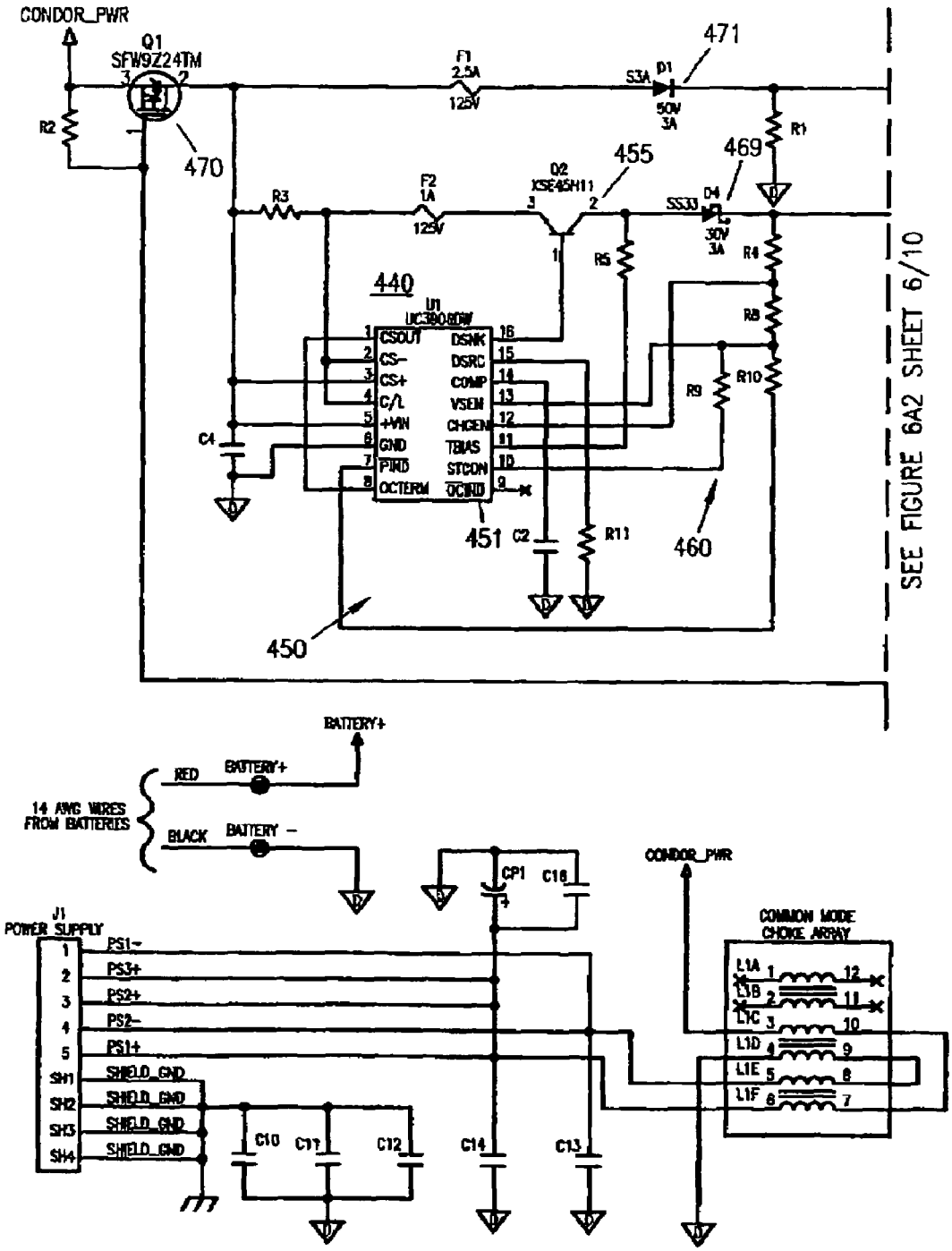
FIG. 6A1

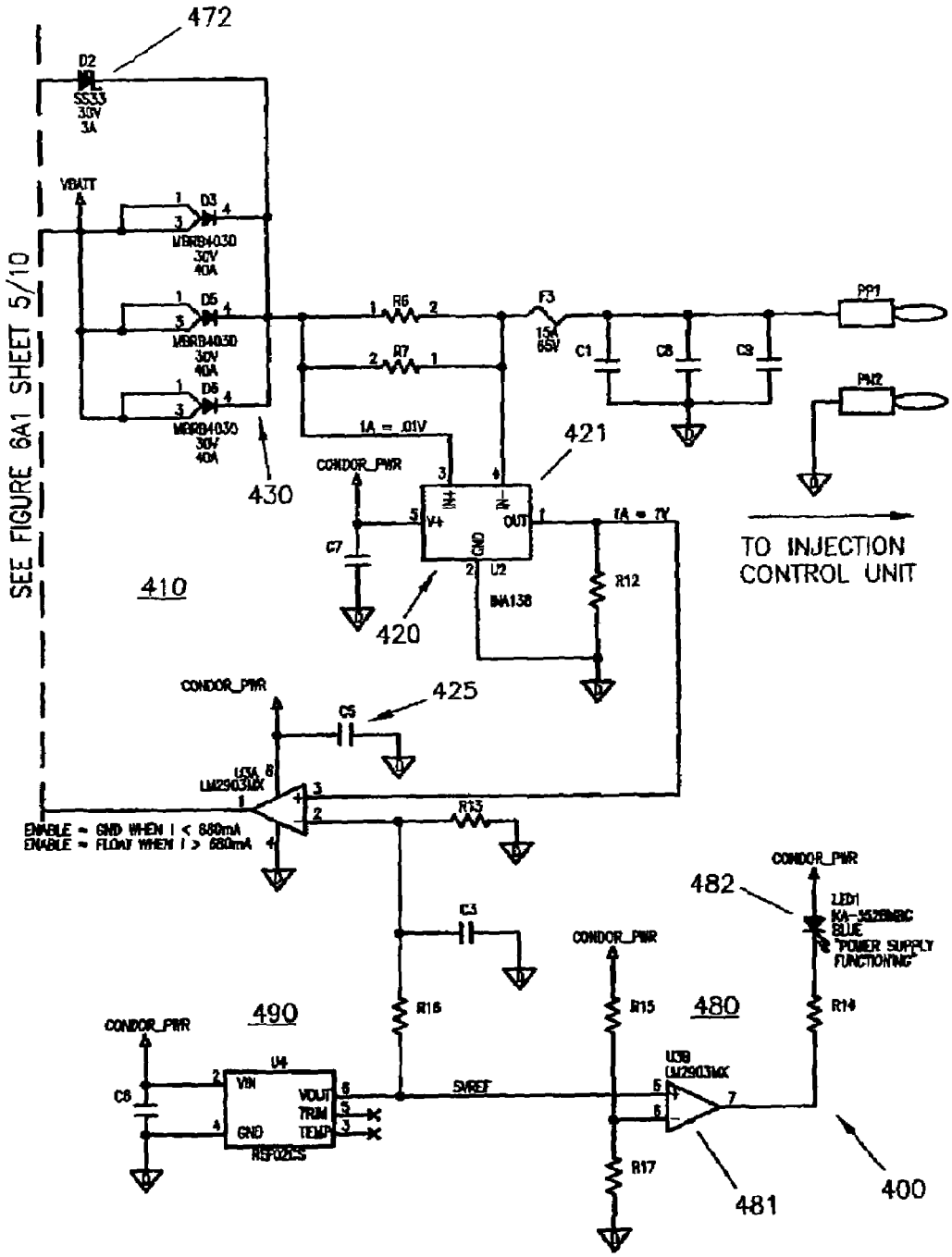
FIG. 6A2

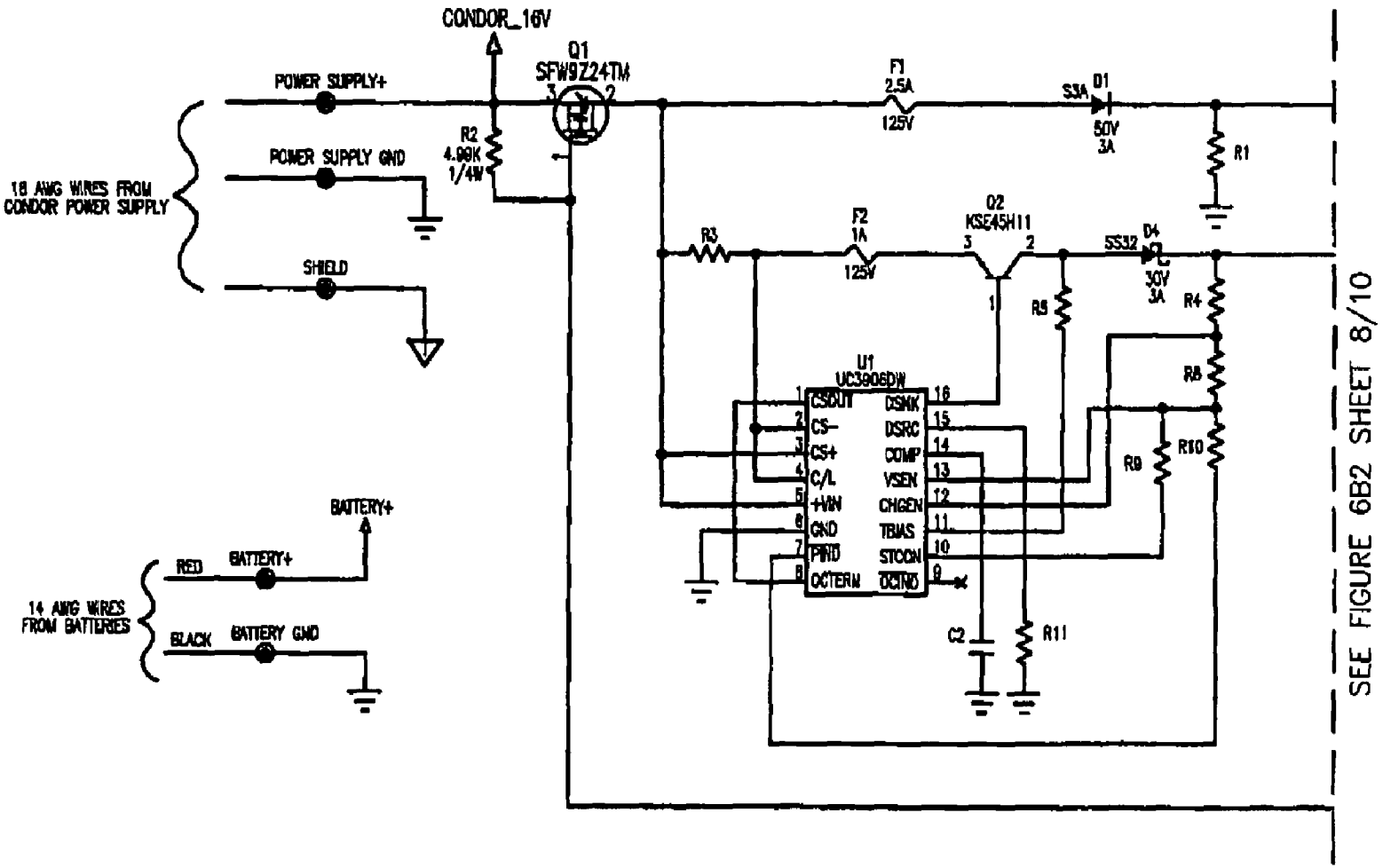
FIG. 6B1

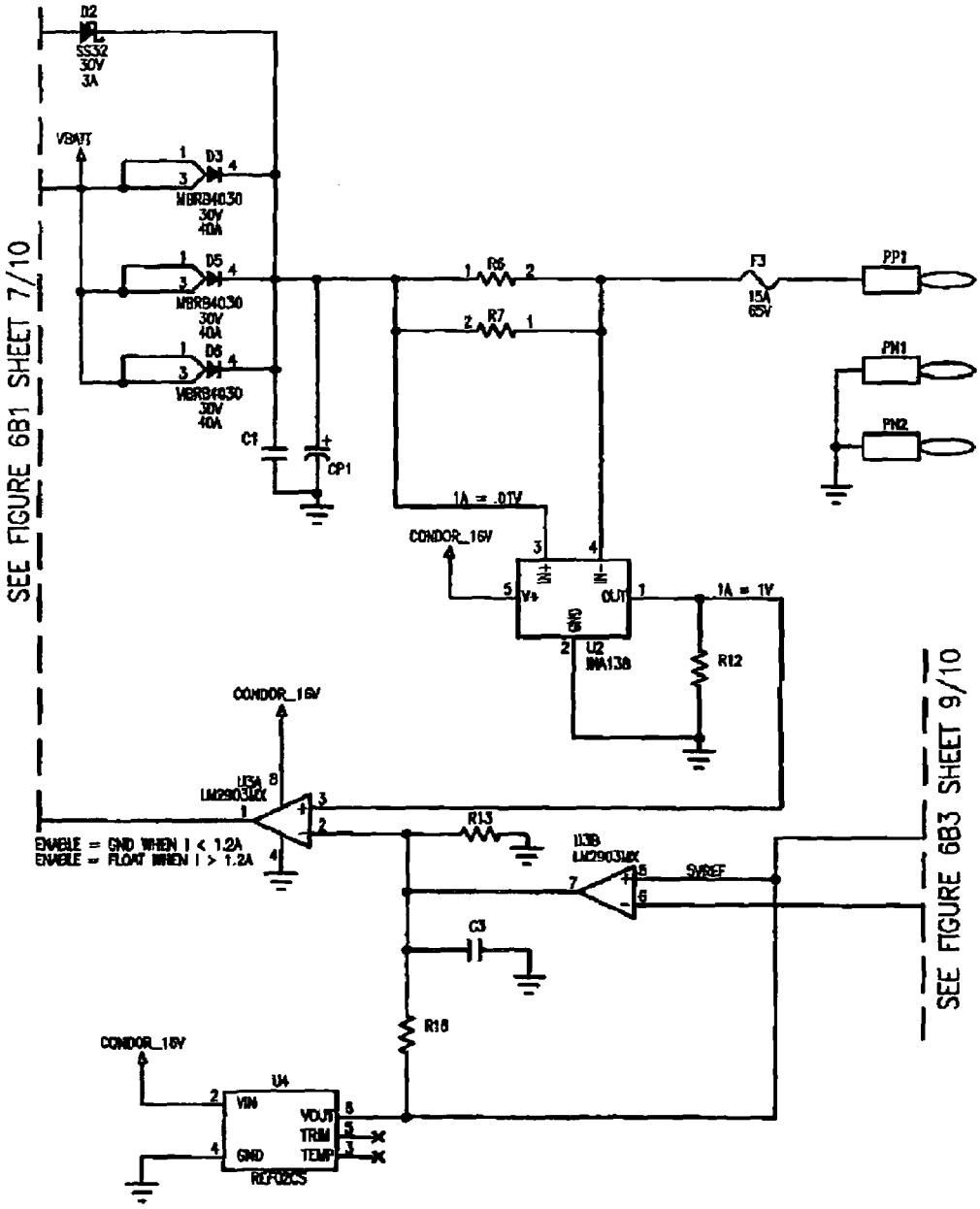
FIG. 6B2

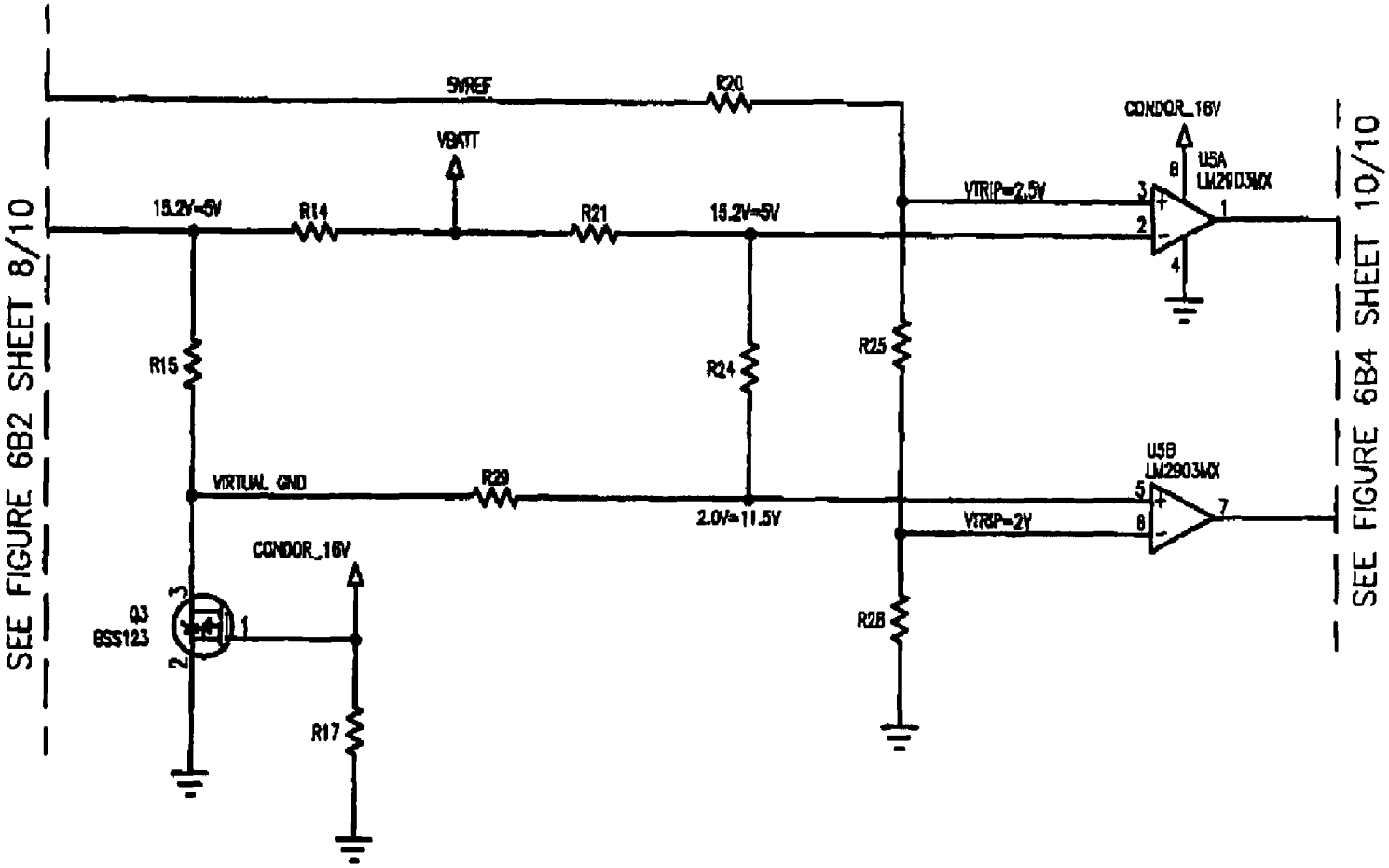
FIG. 6B3

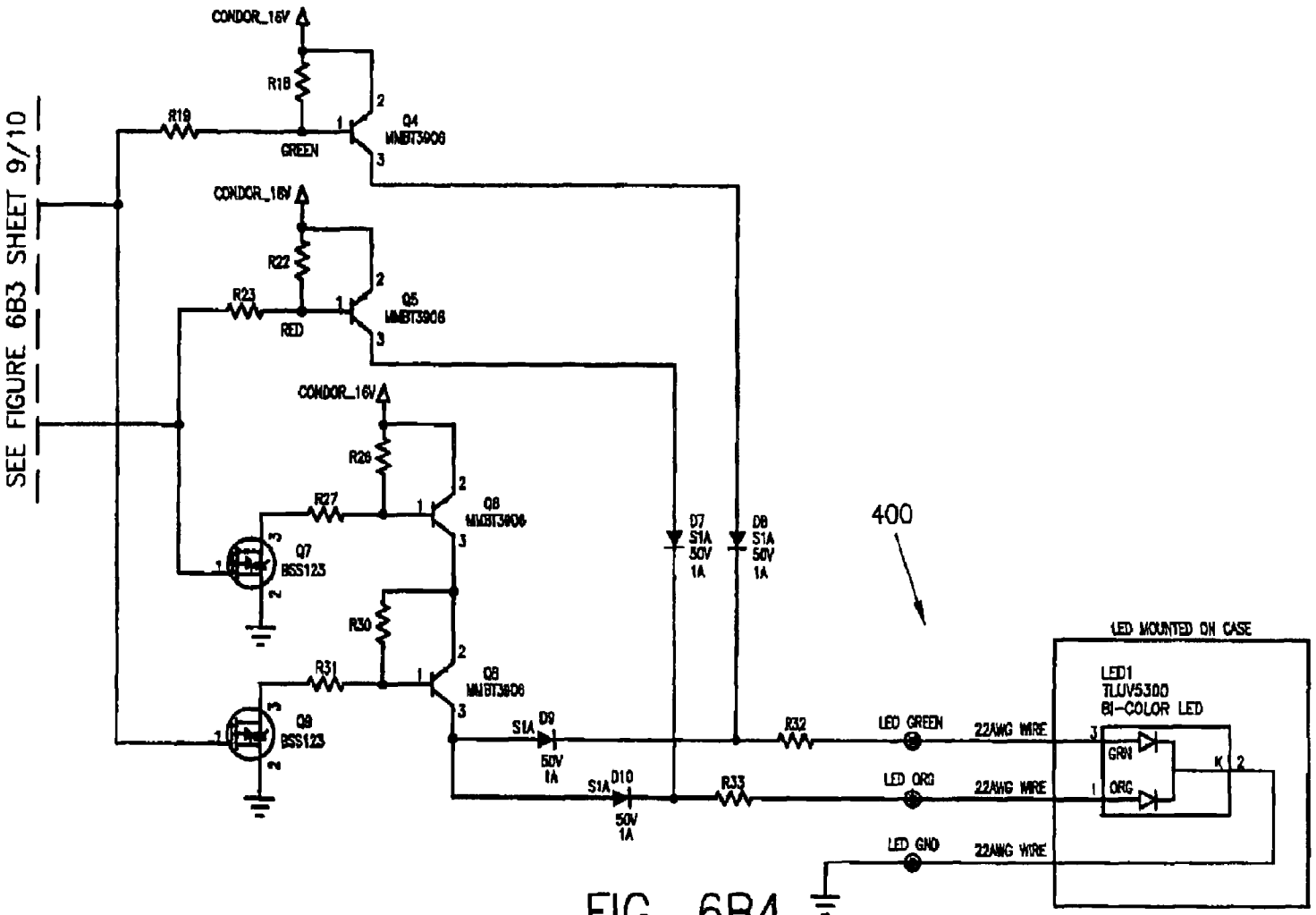
FIG. 6B4

CONTINUOUS BATTERY CHARGER SYSTEM

Matter enclosed in heavy brackets [ ] appears in the original patent but forms no part of this reissue specification; matter printed in italics indicates the additions made by reissue.

CROSS-REFERENCE TO RELATED APPLICATION(S)

This application for patent claims the benefit of U.S. Provisional Application Ser. No. 60/429,511 titled Continuous Battery Charger System, filed Nov. 27, 2002. This provisional application has been assigned to the assignee of the invention disclosed below, and its teachings are incorporated into this document by reference.

FIELD OF THE INVENTION

The invention relates generally to injector systems of the type used with magnetic resonance imaging (MRI) systems to inject contrast media into a patient to enhance the quality of images obtainable during scans of the organs and other internal structures. More particularly, the invention relates to systems and methods of powering such injector systems. Even more particularly, the invention pertains to a continuous battery charger system capable not only of allowing the battery for an injection control unit of such an injector system to power the injection control unit while it is functioning in a non-idle mode of operation but also of charging the battery of such an injection control unit and powering its operations while the injection control unit is functioning in an idle mode of operation.

BACKGROUND OF THE INVENTION

The following information describes one of the many possible environments in which the invention can be used. It is provided to assist the reader to understand the invention, as novel material is often more readily understood if described in a familiar context.

Magnetic resonance imaging (MRI) is a noninvasive method of producing high quality images of the interior of the human body. It allows medical personnel to see inside the body (e.g., organs, muscles, nerves, bones, and other structures) without surgery or the use of potentially harmful ionizing radiation such as X-rays. The images are of such high resolution that disease and other forms of pathology can often be visually distinguished from healthy tissue. Magnetic resonance (MR) systems and techniques have also been developed for performing spectroscopic analyses by which the chemical content of tissue or other material can be ascertained.

MR imaging and spectroscopic procedures are performed in what is known as an MR suite. As shown in FIG. 1A, an MR suite typically has three rooms: a scanner room 1, a control room 2, and an equipment room 3. The scanner room 1 houses the MR scanner 10 into which a patient is moved via a slideable table 11 to undergo a scanning procedure, and the control room 2 contains a computer console 20 from which the operator controls the overall operation of the MR system. In addition to a door 4, a window 5 is typically set in the wall separating the scanner and control rooms to allow the operator to observe the patient during such procedures. The equipment room 3 contains the various subsystems necessary to operate the MR system. The equipment includes a power gradient controller 31, a radio frequency (RF) assembly 32, a spectrometer 33, and a cooling subsystem 34 with which to avoid the build up of heat which, if left unaddressed, could otherwise interfere with the overall performance of the MR system. These subsystems are typically housed in separate cabinets, and are supplied electricity through a power distribution panel 12 as are the scanner 10 and the slideable patient table 11.

An MR system obtains such detailed images and spectroscopic results by taking advantage of a basic property of the hydrogen atom, which is found in abundance in all cells within the body. Within the body's cells, the nuclei of hydrogen atoms naturally spin like a top, or precess, randomly in every direction. When subject to a strong magnetic field, however, the spin-axes of the hydrogen nuclei align themselves in the direction of that field. This is because the nucleus of the hydrogen atom has what is referred to as a large magnetic moment, which is basically an inherent tendency to line up with the direction of the magnetic field to which it is exposed. During an MR scan, the entire body or even just one region thereof is exposed to such a magnetic field. This causes the hydrogen nuclei of the exposed region(s) to line up—and collectively form an average vector of magnetization—in the direction of that magnetic field.

As shown in FIGS. 1B and 1C, the scanner 10 is comprised of a main magnet 101, three gradient coils 103a-c, and, usually, an RF antenna 104 (often referred to as the whole body coil). Superconducting in nature, the main magnet 101 is typically cylindrical in shape. Within its cylindrical bore, the main magnet 101 generates a strong magnetic field, often referred to as the $B_0$ or main magnetic field, which is both uniform and static (non-varying). For a scanning procedure to be performed, the patient must be moved into this cylindrical bore, typically while supine on table 11, as best shown in FIGS. 1B and 1C. The main magnetic field is oriented along the longitudinal axis of the bore, referred to as the z direction, which compels the magnetization vectors of the hydrogen nuclei in the body to align themselves in that direction. In this alignment, the hydrogen nuclei are prepared to receive RF energy of the appropriate frequency from RF coil 104. This frequency is known as the Larmor frequency and is governed by the equation $\omega=YB_0$, where $\omega$ is the Larmor frequency (at which the hydrogen atoms precess), Y is the gyromagnetic constant, and $B_0$ is the strength of the main magnetic field.

The RF coil 104 is generally used both to transmit pulses of RF energy and to receive the resulting magnetic resonance (MR) signals induced thereby in the hydrogen nuclei. Specifically, during its transmit cycle, the coil 104 broadcasts RF energy into the cylindrical bore. This RF energy creates a radio frequency magnetic field, also known as the RF $B_1$ field, whose magnetic field lines point in a direction perpendicular to the magnetization vectors of the hydrogen nuclei. The RF pulse (or $B_1$ field) causes the spin-axes of the hydrogen nuclei to tilt with respect to the main ($B_0$) magnetic field, thus causing the net magnetization vectors to deviate from the z direction by a certain angle. The RF pulse, however, will affect only those hydrogen nuclei that are precessing about their axes at the frequency of the RF pulse. In other words, only the nuclei that "resonate" at that frequency will be affected, and such resonance is achieved in conjunction with the operation of the three gradient coils 103a-c.

Each of the three gradient coils is used to vary the main ($B_0$) magnetic field linearly along only one of the three spatial directions (x,y,z) within the cylindrical bore. Positioned inside the main magnet as shown in FIG. 1C, the gradient coils 103a-c are able to alter the main magnetic field on a very local level when they are turned on and off very rapidly in a specific manner. Thus, in conjunction with the main magnet 101, the gradient coils can be operated according to various imaging techniques so that the hydrogen nuclei—at any given point or in any given strip, slice or unit of volume—will be able to achieve resonance when an RF pulse of the appropriate frequency is applied. In response to the RF pulse, the precessing hydrogen nuclei in the selected region absorb the RF energy being transmitted from RF coil 104, thus forcing the magnetization vectors thereof to tilt away from the direction of the main ($B_0$) magnetic field. When the RF coil 104 is turned off, the hydrogen nuclei begin to release the RF energy they just absorbed in the form of magnetic resonance (MR) signals, as explained further below.

One well known technique that can be used to obtain images is referred to as the spin echo imaging technique. Operating according to this technique, the MR system first activates one gradient coil 103a to set up a magnetic field gradient along the z-axis. This is called the "slice select gradient," and it is set up when the RF pulse is applied and is shut off when the RF pulse is turned off. It allows resonance to occur only within those hydrogen nuclei located within a slice of the region being imaged. No resonance will occur in any tissue located on either side of the plane of interest. Immediately after the RF pulse ceases, all of the nuclei in the activated slice are "in phase," i.e., their magnetization vectors all point in the same direction. Left to their own devices, the net magnetization vectors of all the hydrogen nuclei in the slice would relax, thus realigning with the z direction. Instead, however, the second gradient coil 103b is briefly activated to create a magnetic field gradient along the y-axis. This is called the "phase encoding gradient." It causes the magnetization vectors of the nuclei within the slice to point, as one moves between the weakest and strongest ends of this gradient, in increasingly different directions. Next, after the RF pulse, slice select gradient and phase encoding gradient have been turned off, the third gradient coil 103c is briefly activated to create a gradient along the x-axis. This is called the "frequency encoding gradient" or "read out gradient," as it is only applied when the MR signal is ultimately measured. It causes the relaxing magnetization vectors to be differentially re-excited, so that the nuclei near the low end of that gradient begin to precess at a faster rate, and those at the high end pick up even more speed. When these nuclei relax again, the fastest ones (those which were at the high end of the gradient) will emit the highest frequency of radio waves and the slowest ones emit the lowest frequencies.

The gradient coils 103a-c therefore allow these radio waves to be spatially encoded, so that each portion of the region being imaged is uniquely defined by the frequency and phase of its resonance signal. In particular, as the hydrogen nuclei relax, each becomes a miniature radio transmitter, giving out a characteristic pulse that changes over time, depending on the local microenvironment in which it resides. For example, hydrogen nuclei in fats have a different microenvironment than do those in water, and thus emit different pulses. Due to these differences, in conjunction with the different water-to-fat ratios of different tissues, different tissues emit radio signals of different frequencies. During its receive cycle, RF coil 104 detects these miniature radio emissions, which are often collectively referred to as the MR signal(s). From the RF coil 104, these unique resonance signals are conveyed to the receivers of the MR system where they are converted into mathematical data. The entire procedure must be repeated multiple times to form an image with a good signal-to-noise ratio (SNR). Using multidimensional Fourier transformations, the MR system then converts the mathematical data into a two- or even a three-dimensional image of the body, or region thereof, that was scanned.

As shown partially in FIG. 1A, the scanner room 1 is shielded to prevent the entry and exit of electromagnetic waves. Specifically, the materials and design of its ceiling, floor, walls, door, and window effectively form a barrier or shield 6 that prevents the electromagnetic signals generated during a scanning procedure (e.g., the RF energy) from leaking out of scanner room 1. Likewise, shield 6 is designed to prevent external electromagnetic noise from leaking into the scanner room 1. The shield 6 is typically composed of a copper sheet material or some other suitable conductive layer. The window 5, however, is typically formed by sandwiching a wire mesh material between sheets of glass or by coating the window with a thin layer of conductive material to maintain the continuity of the shield. The conductive layer also extends to the door 4, which when open allows access to the scanner room 1 and yet when closed is grounded to and constitutes a part of shield 6. The ceiling, floor, walls and door of shield 6 provide approximately 100 decibels (dB) of attenuation, and window 5 approximately 80 dB, for the typical operating range of MR scanners (~20 to 200 MHz). Barrier 6 thus shields the critical components (e.g., scanner, preamplifiers, receivers, local coils, etc.) of the MR system from undesirable sources of electromagnetic radiation (e.g., radio signals, television signals, and other electromagnetic noise present in the local environment).

The shield 6 serves to prevent external electromagnetic noise from interfering with the operation of the scanner 10, which if not addressed could otherwise result in degradation of the images and/or spectroscopic results obtained during the scanning procedures. For the scanner 10 to operate, however, the shield 6 must still allow communication of data and control signals between the scanner room 1 and the control and equipment rooms 2 and 3, and such communication is generally accomplished through a penetration panel 16.

As shown in FIG. 1A, the penetration panel 16 is typically incorporated into the wall between the scanner and equipment rooms 1 and 3. It features several ports through which the scanner 10 and other devices in the scanner room 1 are connected by cables to the computer console 20 and control subsystems in the control and equipment rooms 2 and 3, respectively. Each port typically includes a filtered BNC connector, which allows the communication of data and/or control signals while still maintaining the barrier to unwanted electromagnetic signals.

Several auxiliary systems designed for use in the MR suite require communication across the shield 6. These systems are typically bifurcated, i.e., they have two pieces of equipment, with one piece located in the scanner room 1 and the other situated in the control room 2. One example is the Spectris® MR Injector System produced by Medrad, Inc., of Indianola, Pa. It allows contrast media to be injected into the blood stream of a patient undergoing an MR procedure. (As is well known, contrast media serves to increase the contrast between the different types of tissues in the region of the body undergoing a scan, and thereby enhances the resolution of the images obtained during the scan.) In this bifurcated system, an injection control unit in the scanner room 1 with which to inject the contrast media into the patient requires communication with a controller therefor situated in the control room 2. This is disclosed in U.S. Pat. No. 5,494,036 to Uber, III et al., incorporated herein by reference. The '036 patent discloses that the injection control unit and its controller communicate across shield 6 using a pair of transceivers attached to, and aimed at each other through, opposite sides of window 5. They allow the injection control unit and controller to communicate, via the transceivers and their associated fiber optic cables, at frequencies (e.g., infrared or visual) that readily penetrate the shield 6 yet do not adversely affect the operation of the MR system.

The Spectris® Solaris™ MR Injector System, which is also produced by Medrad, Inc., uses a fiber optic link only, without resort to transceivers, to convey its data and control signals across the barrier 6. As shown in FIG. 2, this injector system has its fiber optic cable 13 routed through the shield 6 (i.e., preferably through one of the tuned ports in penetration panel 16) to enable optical communication between its injection control unit 50 and its controller 60. Because the communications links of the aforementioned injector systems are implemented optically, they do not introduce any potentially troublesome RF interference into the scanner room 1 as would be the case if standard wire cabling were used.

More relevant to the invention disclosed below, several prior art injector systems use batteries to supply power to their injection control units rather than AC power. One disadvantage of running AC power cords in the scanner room 1, particularly if close to the scanner 10, is that unless heavily shielded they tend to radiate RF emissions, which can interfere with the operation of the scanner 10 and cause artifacts to appear in the resulting images. The Spectris® Solaris™ MR Injector System, for example, as shown in FIG. 2, has its injection control unit 50 powered with a battery pack 40 that plugs into a corresponding socket 52 within the lower console housing 51. The battery pack 40 is rechargeable through use of a separate battery charger 41, as shown in FIG. 3.

Although it reduces the likelihood of tripping accidents due to the absence of power cords in the scanner room 1, the use of a stand-alone battery pack still poses several disadvantages to the operators of injector systems so equipped. First, the operator must regularly monitor the state of charge of the battery packs, which can generally be done in conjunction with most injector systems. If a battery pack with a low state of charge is not detected in a timely fashion, however, the scanning procedure will have to be delayed while the depleted battery pack in the injection control unit is swapped for a fully-charged one from the battery charger. At hospitals and other sites that routinely perform high numbers of contrast-enhanced procedures, such delays are particularly burdensome, as the battery packs must be swapped relatively often. Such delays inevitably reduce the number of patients that can be scanned in any given time period. This not only decreases the amount of revenue that can be derived from the MR suite but also ultimately imposes greater overall costs on the providers, and hence users, of medical services.

The Optistar™ Injector System, produced by the Liebel-Flarsheim Company of Mallinckrodt Inc., a division of Tyco International Ltd., attempts to overcome these disadvantages by routing DC power from the control or equipment rooms 2 and 3 through penetration panel 16 into the scanner room 1. As disclosed in U.S. Patent Application Publication No. 2002/0169415, situated in the control room is a power supply, which has an off-the-shelf AC/DC converter and a standard data link incorporated into one box. At its input, the AC/DC converter plugs into either a 115v AC outlet or a 240v AC outlet. An RF shielded cable from the power supply box routes power conductors (which carry DC power from the output of the AC/DC converter) and data conductors (which carry data and control signals to and from the computer console) through the penetration panel into the scanner room. The power conductors are connected directly to existing wiring within the battery compartment of the injection control unit, thereby eliminating the need for batteries which were necessary to operate an earlier pre-power supply version of the Optistar™ Injector System. In the Optistar™ Service and Parts Manual 801993-A (April 2001) with amended Installation Instructions 801995-A (May 2001), the power supply box is shown deployed in either the control room or the equipment room.

The advantage of such a power supply scheme is that heavy users of such injector systems do not have to contend with the task of swapping batteries. Although this scheme provides an uninterrupted supply of DC power to the injection control unit, it denies the user the increased mobility that an injection control unit has in the scanner room when powered by batteries. This shortcoming is but one of several that the Liebel-Flarsheim power supply scheme exhibits when compared to the invention disclosed below. The advantages of the invention herein presented will become fully apparent to persons skilled in the relevant art from a reading of the detailed description section of this document, and will become particularly apparent when the detailed description is considered along with the drawings and claims presented herein.

SUMMARY OF THE INVENTION

The objectives and advantages of the invention are attained by the various embodiments and related aspects of the invention summarized below.

In a presently preferred embodiment, the invention provides a battery charger system for an injector system that has an idle mode of operation and a non-idle mode of operation. The battery charger system comprises a first power cord, an AC/DC converter, a second power cord, and a battery pack. The first power cord is for conveying AC power from a source thereof. The AC/DC converter is used to convert the AC power received from the first power cord to DC power. The second power cord is used to convey the DC power received from an output of the AC/DC converter. The battery pack includes a battery and a charging module. The charging module is for receiving the DC power from the AC/DC converter via the second power cord and for monitoring the operating mode of the injector system. When the injector system is operating in the idle mode, the charger module provides DC power received from the AC/DC converter to the battery for the charging thereof. When the injector system is operating in the non-idle mode, the charger module prevents DC power from the AC/DC converter from reaching the battery and thus enables the battery to provide DC power to the injector system.

In a related aspect, the charger module also provides DC power received from the AC/DC converter to the injector system when the injector system is operating is the idle mode.

In a related embodiment, the invention also provides a battery charger system for use with an injection control unit of an injector system. The battery charger system comprises an AC/DC converter and a battery pack. The AC/DC converter is used to convert AC power from a source thereof to DC power. The battery pack includes a battery and a charging module. The charging module is for monitoring an operating mode of the injector system. When the battery pack is disconnected from the injection control unit, the charging module enables the AC/DC converter to charge the battery with the DC power therefrom. When the battery pack is connected to the injection control unit: (A) upon detecting the injector system in an idle mode of operation, the charger module routes the DC power from the AC/DC converter to both the battery for the charging thereof and the injection control unit for operation thereof; and (B) upon detecting the injector system in a non-idle mode of operation, the charger module prevents the AC/DC converter from charging the battery and enables the battery to provide DC power to the injection control unit.

In a related aspect, the invention also provides a charging module for a battery for use with an injection control unit of an injector system. The charging module comprises an output selector stage, a charging stage, and an indicator stage. The output selector stage is for sensing the mode of operation of the injection control unit and for providing a turn-on signal when the injection control unit is operating in an idle mode and a turn-off signal when the injection control unit is operating in a non-idle mode. The charging stage is connected to the output selector stage. Upon receiving the turn-off signal, the charging stage prevents the battery from being charged by a power supply therefor and enables the battery to provide DC power to the injection control unit. Upon receiving the turn-on signal, the charging stage enables DC power from the power supply to be conveyed to the injection control unit and assumes either a low current charging mode or a multi-state charging mode. When a voltage level of the battery is less than a preselected minimum level, the charging stage assumes the low current charging mode wherein the charging stage charges the battery with a charging current limited to a trickle level. When the voltage level of the battery is the preselected minimum level or greater, the charging stage assumes the multi-state charging mode wherein the charging stage operates according to (I) a bulk-charge state, when the voltage level of the battery is the preselected minimum level or greater yet below a set percentage of an overcharge level, wherein the charging stage charges the battery with a charging current at a peak level thereof; (II) an over-charge state, when the voltage level of the battery is equal to or exceeds the set percentage of the overcharge level, wherein the charging stage continues charging the battery until the charging current falls to a minimum threshold; and (III) a standby state, when the charging current falls below the minimum threshold, wherein the charging stage applies a constant voltage to the battery until the voltage level of the battery drops at least a specified percentage below a float level upon which the charging stage will commence operating according to the bulk-charge state. The indicator stage is for indicating when the power supply is capable of providing to the charging module sufficient power to efficiently charge the battery.

The invention also provides an injector system comprising an injection control unit, a controller, and a battery charger system. The injection control unit is for use in injecting a medicinal substance into a patient. The controller is for controlling the operation of the injector system inclusive of whether the injector system operates in an idle mode of operation or a non-idle mode of operation. The battery charger system is for providing power to the injection control unit. The battery charger system comprises a power supply and a battery pack. The power supply is for converting AC power from a source thereof to DC power. The battery pack includes a battery and a charging module. The charging module is for monitoring the mode of operation of the injector system. When the battery pack is disconnected from the injection control unit, the charging module enables the power supply to charge the battery with the DC power therefrom. When the battery pack is connected to the injection control unit: (A) upon detecting the injector system in the idle mode, the charger module routes the DC power from the power supply to both the battery for the charging thereof and the injection control unit for operation thereof; and (B) upon detecting the injector system in the non-idle mode, the charger module prevents the power supply from charging the battery and enables the battery to provide DC power to the injection control unit.

The invention further provides a battery charger system for use with a battery-powered system. The battery charger system comprises a power supply and a battery pack. The power supply is for supplying DC power. The battery pack includes a battery and a charging module. The charging module is connectible to the power supply for receiving the DC power therefrom and is capable of monitoring an operating mode of the battery-powered system when linked thereto. When the battery pack is disconnected from the battery-powered system, the charging module enables the power supply to charge the battery with the DC power therefrom. When the battery pack is connected to the battery-powered system: (A) upon detecting the battery-powered system in an idle mode of operation, the charger module routes the DC power from the power supply to both the battery for the charging thereof and the battery-powered system for operation thereof; and (B) upon detecting the battery-powered system in a non-idle mode of operation, the charger module prevents the power supply from charging the battery and enables the battery to provide DC power to the battery-powered system.

In a related aspect, the invention also provides a charging module for a battery for use with a battery-powered system. The charging module comprises an output selector stage and a charging stage. The output selector stage is for sensing the current drawn by the battery-powered system and for providing a turn-on signal when the current is less than a predetermined level and a turn-off signal when the current is greater than the predetermined level. The charging stage is connected to the output selector stage. Upon receiving the turn-off signal, the charging stage prevents the battery from being charged by a power supply therefor and enables the battery to provide DC power to the battery-powered system. Upon receiving the turn-on signal, the charging stage enables DC power from the power supply to be conveyed to the battery-powered system and assumes either a low current charging mode or a multi-state charging mode. When a voltage level of the battery is less than a preselected minimum level, the charging stage assumes the low current charging mode wherein the charging stage charges the battery with a charging current limited to a trickle level. When the voltage level of the battery is the preselected minimum level or greater, the charging stage assumes the multi-state charging mode wherein the charging stage operates according to (I) a bulk-charge state, when the voltage level of the battery is the preselected minimum level or greater yet below a set percentage of an overcharge level, wherein the charging stage charges the battery with a charging current at a peak level thereof; (II) an over-charge state, when the voltage level of the battery is equal to or exceeds the set percentage of the overcharge level, wherein the charging stage continues charging the battery until the charging current falls to a minimum threshold; and (III) a standby state, when the charging current falls below the minimum threshold, wherein the charging stage applies a constant voltage to the battery until the voltage level of the battery drops at least a specified percentage below a float level upon which the charging stage will commence operating according to the bulk-charge state.

BRIEF DESCRIPTION OF THE DRAWINGS

The invention, and particularly its presently preferred and alternative embodiments and related aspects, will be better understood by reference to the detailed disclosure below and to the accompanying drawings, in which:

FIG. 6A is a schematic circuit diagram of the charging module according to the preferred embodiment of the invention.

FIG. 6B is a schematic circuit diagram of the charging module according to another embodiment of the invention.

Figure 1A:
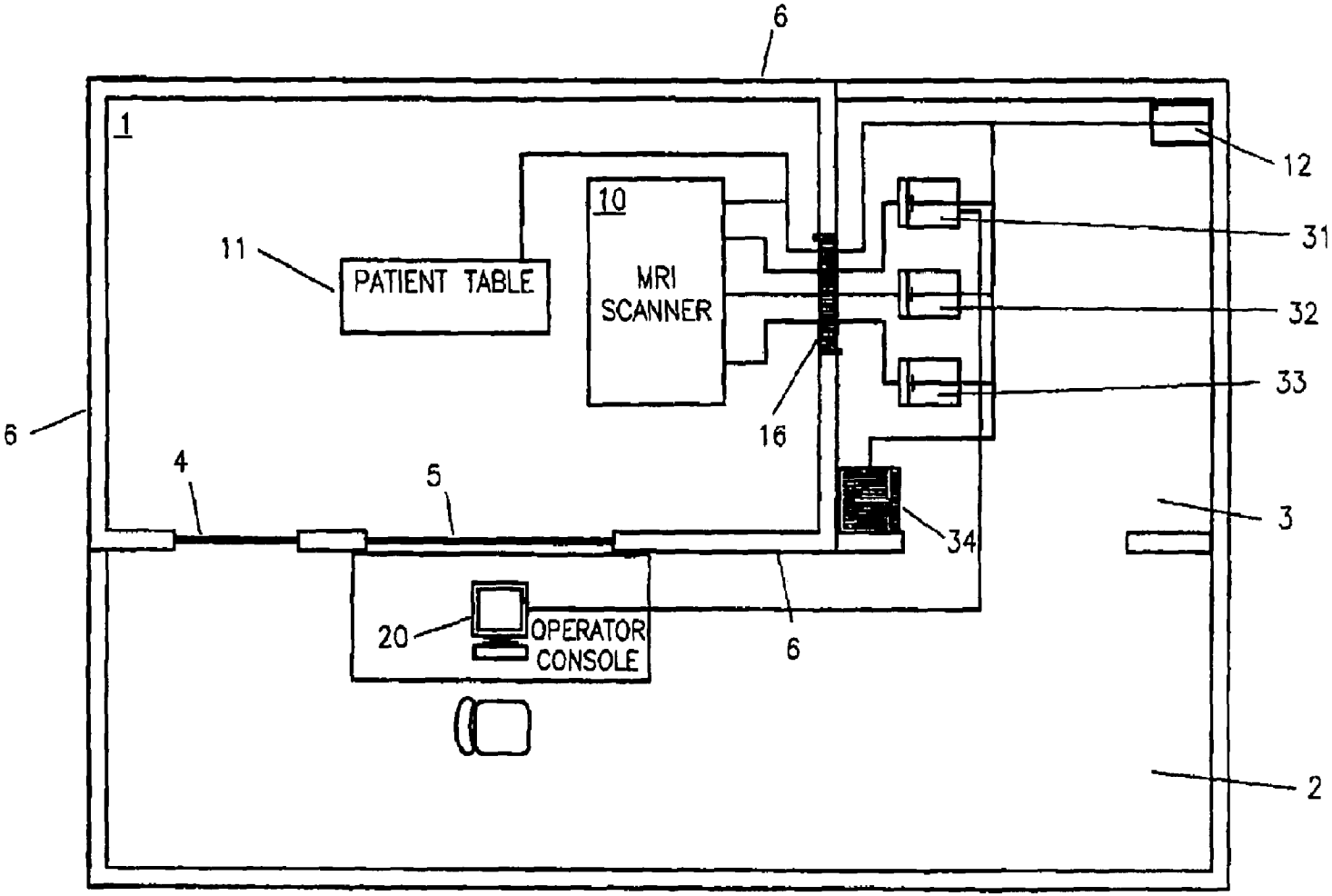
FIG. 1A illustrates the layout of an MR suite inclusive of the scanner room in which the scanner and patient table are located, the control room in which the computer console for controlling the scanner is situated, and the equipment room in which various control subsystems for the scanner are sited.
Figure 1B:
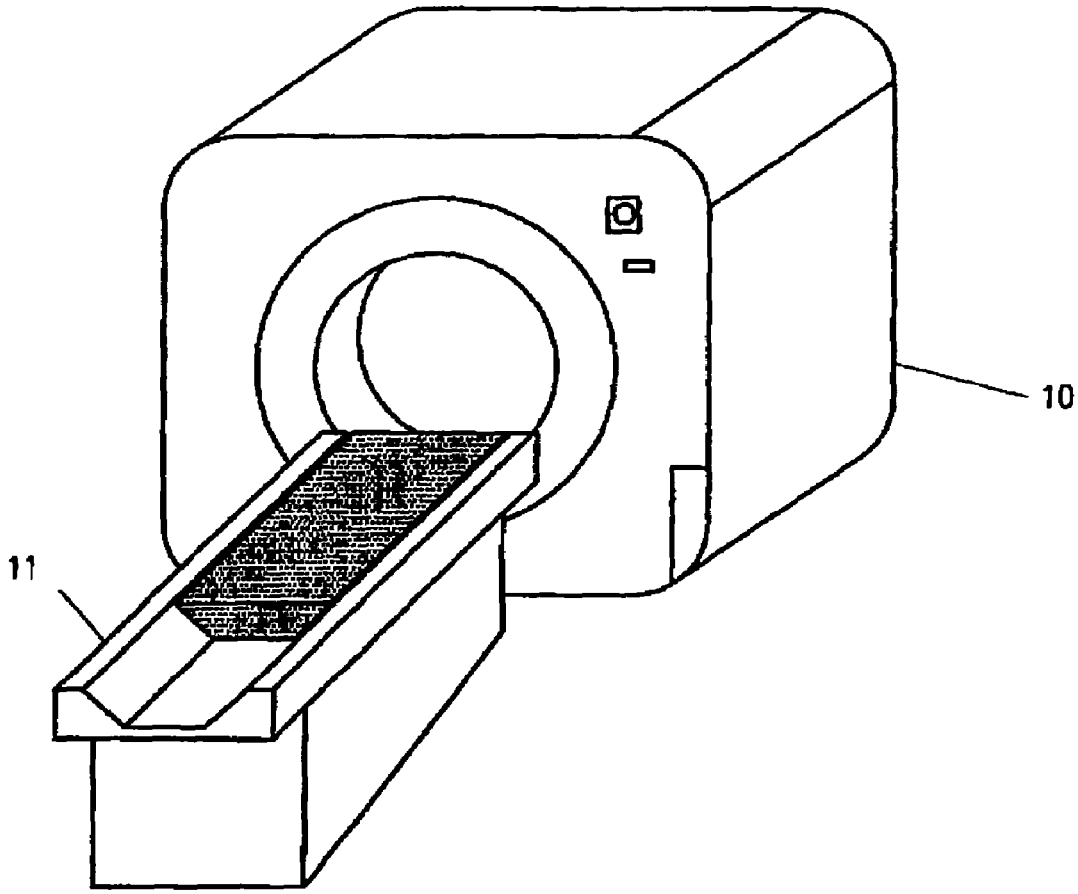
FIG. 1B shows a scanner and patient table of the type shown schematically in FIG. 1A.
Figure 1C:
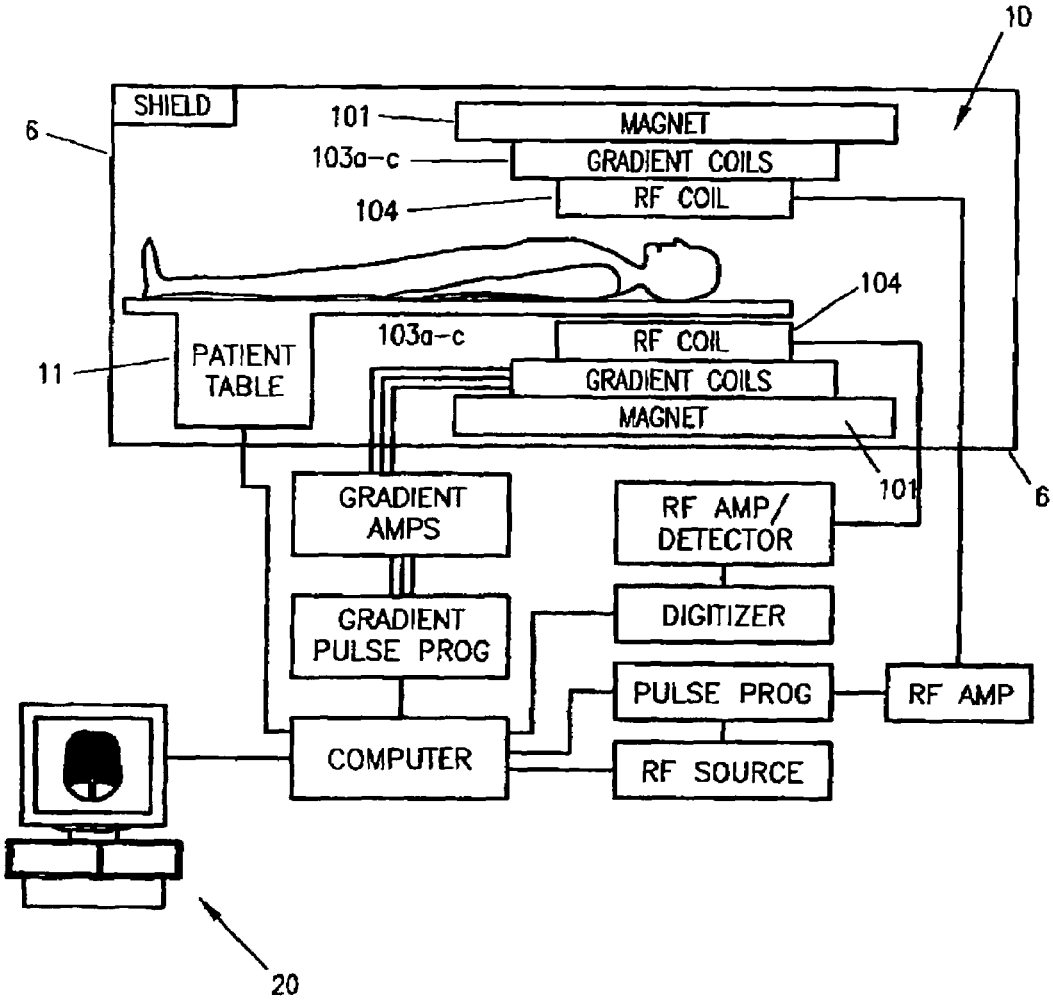
FIG. 1C is a more detailed view of the MR system shown in FIGS. 1A and 1B showing the computer console and the various subsystems located in the control and equipment rooms and a cross-section of the scanner and patient table situated in the scanner room.
Figure 3:
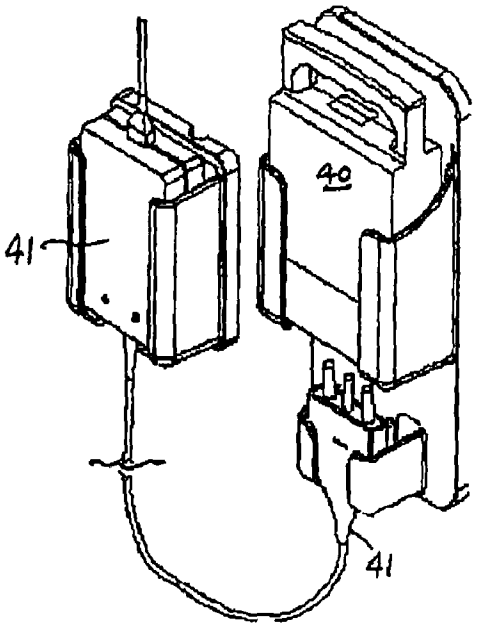
FIGURE 3 (Prior Art)
FIG. 3 illustrates a battery charger for the prior art battery pack of FIG. 2.
Figure 2:
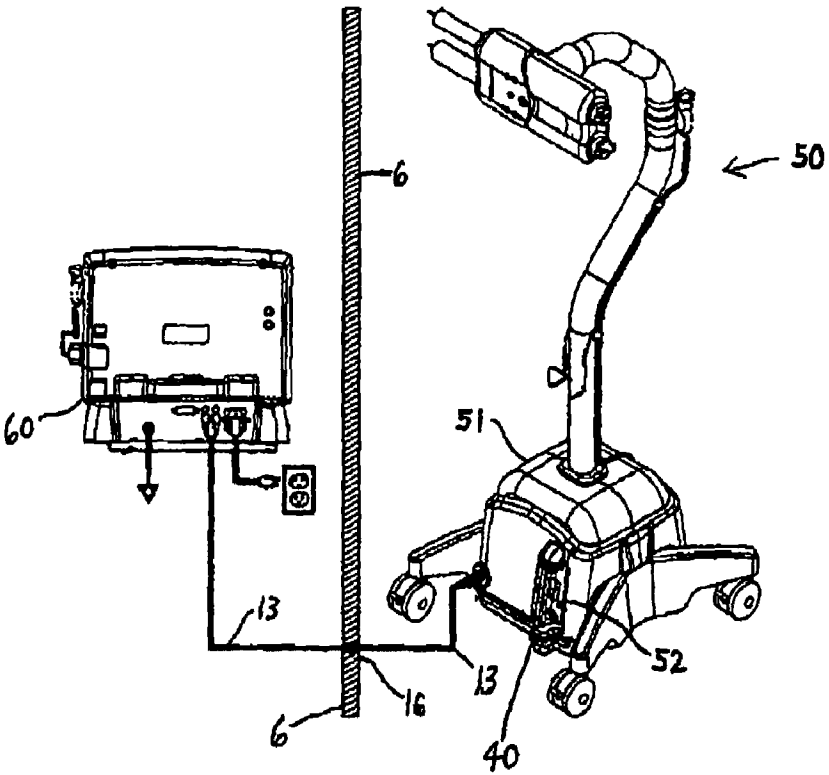
FIGURE 2 (Prior Art)
FIG. 2 illustrates a prior art MR injector system showing (i) its injection control unit in the scanner room and its controller in the control room linked via the penetration panel through which they communicate and (ii) a prior art battery pack that plugs into a corresponding socket within the injection control unit by which it is supplied with DC power.

DETAILED DESCRIPTION OF THE PRESENTLY PREFERRED AND ALTERNATIVE EMBODIMENTS OF THE INVENTION

Although the invention herein described and illustrated is presented in the context of injector systems designed for use in the MR environment, the reader will understand that the invention can be applied or adapted not only to a wide variety of other systems but also to various other types of environments. The presently preferred embodiment and related aspects of the invention will now be described with reference to the accompanying drawings, in which like elements have been designated where possible by the same reference numerals.

FIGS. 4-6B illustrate the invention, namely, a continuous battery charger (CBC) system, generally designated 100. The CBC system 100 includes an AC power cord 110, a power supply 120, a DC power cord 130, and a battery pack 140. The CBC system 100 is described below in the context of an injection control unit 50 for the Spectris® Solaris™ injector system, although it is equally applicable to other systems and environments as noted above.

Figure 4:
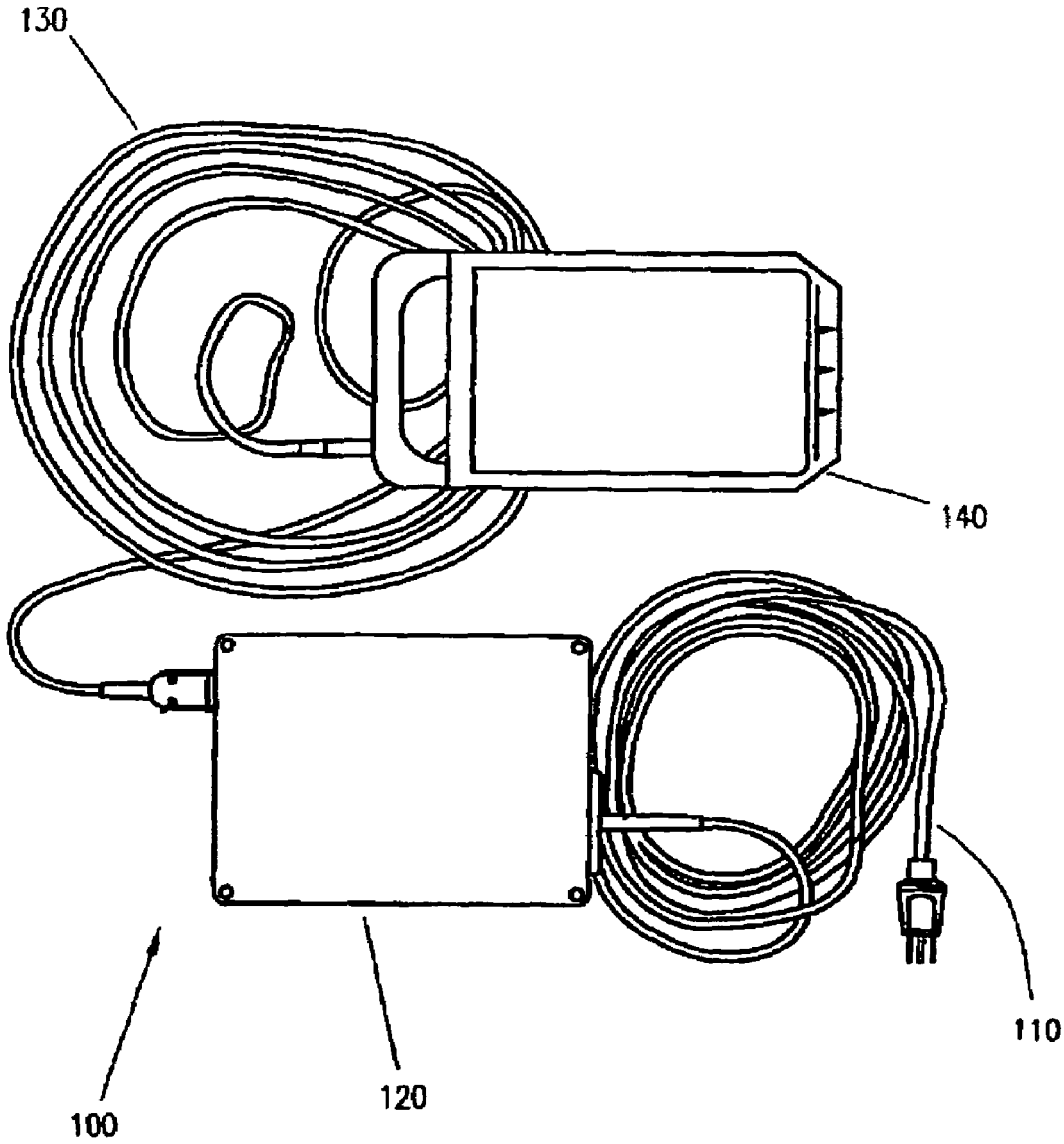
FIG. 4 illustrates a preferred embodiment of the invention, showing a power supply and an AC power cord therefor, a battery pack, and a DC power cord interconnecting them.

The power supply 120 may take the form of an AC/DC converter such as the GLM65-15 medical grade switcher manufactured by Condor Power Supplies, Inc., of Oxnard, Calif. As disclosed in Condor Publication No. 41-34796-0001 Rev. E (Jul. 30, 2002) and the data sheet(s) corresponding thereto, incorporated herein by reference, the GLM65-15 power supply is capable of providing 65 Watts (W) at 15 Volts (V) DC from an input of 90-264V AC. Although the CBC system 100 in its preferred embodiment requires approximately only 20.96 W when used with the Spectris® Solaris™ injector system, the GLM65-15 was chosen at least partly because of its use in other injector systems produced by Medrad, Inc. Those skilled in the design and development of injector systems and associated circuitry realize, of course, that the particular power supply chosen need only meet the power requirements of the specific injector system with which it is used. The GLM65-15 power supply also provides the CBC system 100 with protection against short circuits and overloading at its output. FIG. 4 shows the AC and DC power cords 110 and 130 connected to opposite ends of power supply 120.

Figure 5B:
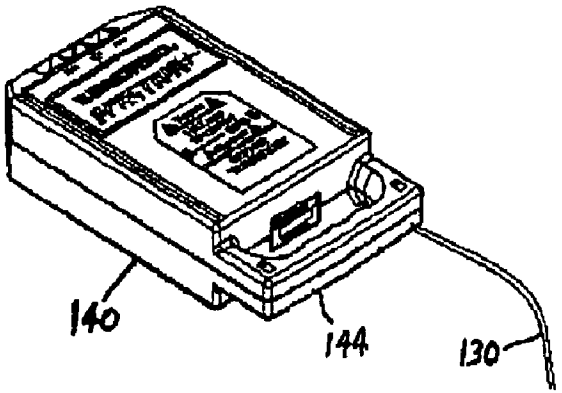
FIG. 5B is a perspective view of the battery pack of FIG. 5A in its fully assembled state.
Figure 5C:
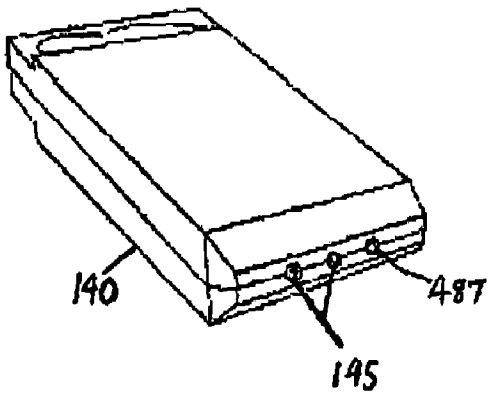
FIG. 5C is a perspective view of the battery pack of FIG. 5A from its opposite end.
Figure 5A:
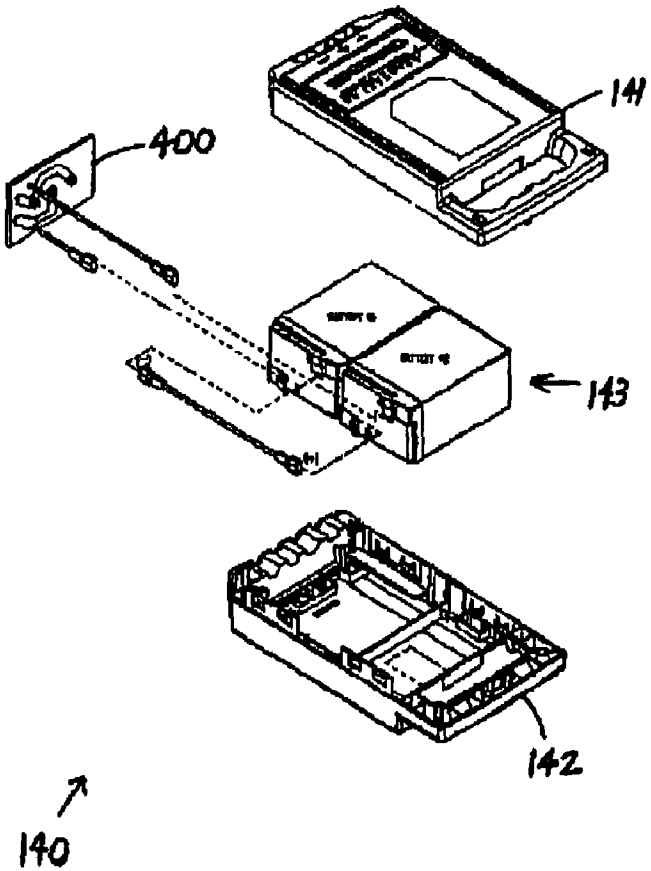
FIG. 5A is an exploded view of the battery pack depicted in FIG. 4, showing the upper and lower halves of its case and the batteries and charging module enclosed therein.

As best shown in FIG. 5A, the battery pack 140 includes at least one battery 143 and a charging module 400. For the preferred application of injection control unit 50, the battery pack preferably includes two Model BP5-6 lead-acid batteries produced by the B.B. Battery Co., Ltd. The two BP5-6 batteries are shown connected in series to charging module 400. The batteries 143 and charging module 400 are contained within a single case comprised of first and second halves 141 and 142. As shown in FIG. 5B, the DC power cord 130 preferably connects to the charging module through the handle 144 of battery pack 140. FIG. 5C shows the other end of the battery pack 140 at which the output terminals 145 of the battery pack are situated. When the battery pack 140 is plugged into the socket 52 of console 51 of injection control unit 50, the output terminals 145 contact the corresponding battery contacts within the injection control unit 50 to provide DC power thereto. FIG. 5C also shows an indicator light 487 with which to signify the operational state of the invention.

When the battery pack 140 is plugged into injection control unit 50, the charging module 400 allows the power supply 120 not only to charge the batteries 143 but also to provide power to the injection control unit while it is functioning in its standby or idle mode of operation. The charging module 400 does not, however, allow DC power from power supply 120 to power the injection control unit while it is operating in its non-idle mode of operation. When operating in its non-idle mode, the injection control unit 50 gets its power only from the batteries 143. Conversely, when battery pack 140 is unplugged from injection control unit 50, the charging module 400 still allows power supply 120 to charge the batteries 143. Furthermore, when power supply 120 is disconnected from battery pack 140, the charging module 400 enables the batteries to provide power to injection control unit 50 regardless of its mode of operation.

The charging module 400 includes an output selector stage 410, a charging stage 440, an indicator stage 480, and a regulator stage 490, all of which described herein in the context of its presently preferred embodiment shown in FIG. 6A. An alternative embodiment of the charger module 400 is illustrated in FIG. 6B.

The regulator stage 490 may be implemented using any one of a variety of regulator circuits known in the electrical/electronic arts. The regulator illustrated in FIG. 6A, for example, is a precision voltage reference produced and sold under Model No. REF02 by Analog Devices, Inc., of Norwood, Mass. As disclosed in Rev. C (2002) of its specification sheet, incorporated herein by reference, the REF02 regulator 490 is capable of providing a stable 5V DC output, regulated to approximately ±1%, from the 15V DC input received from the GLM65-15 power supply 120 via DC power cord 130. This 5V DC reference voltage is supplied to both the output selector stage 410 and the indicator stage 480.

The output selector stage 410 includes a current monitoring circuit 420, a comparator circuit 425, and one or more Schottky Barrier rectifying diodes 430. The current monitoring circuit 420 can take the form of a current shunt monitor 421 such as the INA138 chip made by Texas Instruments Inc., as disclosed in Datasheet SBOS122A (Rev. 12-2002), incorporated herein by reference. The comparator circuit 425 can be implemented with the LM2903MX differential comparator chip produced by Fairchild Semiconductor Corporation. As shown in FIG. 6A, both chips are powered with 15V DC received from the GLM65-15 power supply 120.

The current shunt monitor 421 has its $V_{IN-}$ input connected to the external load, which in this preferred application is injection control unit 50. Resistors $R_6$ and $R_7$, acting as current sampling resistors, are connected in parallel across inputs $V_{IN+}$ and $V_{IN-}$. The output of chip 421 is connected to an external load resistor $R_{12}$. Differential comparator 425 has its positive input connected to the output or OUT terminal of current shunt monitor 421 and its negative input connected to the regulator 490 through a resistor divider network, $R_{13}$ and $R_{16}$. The Schottky Barrier diodes 430 are connected in parallel between the $V_{IN+}$ input of current monitor chip 421 and the positive ($V_{Batt}$) terminal of batteries 143.

The resistors $R_6$ and $R_7$ are used by chip 421 to monitor the current drawn by injection control unit 50, whether it is drawn from the batteries 143 ($V_{Batt}$) via the Schottky Barrier diodes 430 or from the power supply 120 via transistor 470, series diode 471 and Schottky diode 472. The differential input voltage that the current shunt monitor 421 detects at its inputs $V_{IN+}$ and $V_{IN-}$, via resistors $R_6$ and $R_7$, is converted to an interim current and delivered to the OUT terminal of chip 421. This current is then converted back to a voltage by external load resistor $R_{12}$ at the OUT terminal. For the preferred application of injection control unit 50, sampling resistors $R_6$ and $R_7$ and load resistor $R_{12}$ are preferably selected so that the current flowing to injection control unit 50 if less than 680 mA yields a corresponding output voltage of less than 0.68V and if greater than 680 mA yields a corresponding output voltage of greater than 0.68V (i.e., 1A≈1V). The 680 mA level was chosen because when injection control unit 50 draws less it is functioning in its idle or standby mode of operation. Conversely, when it draws more than that predetermined level, the injection control unit is functioning in its non-idle mode of operation.

The resistor divider network of comparator circuit 425 steps down the 5V DC received from regulator 490 to a nominal reference voltage. For the preferred application of injection control unit 50, resistors $R_{13}$ and $R_{16}$ are selected so that a reference voltage of 0.68V exists at the negative terminal of the comparator chip 425. The output of the comparator chip thus depends on the voltage output by the current monitor chip 421 at its OUT terminal. When the output voltage at its positive input is less than 0.68V, the comparator chip 425 outputs a low level logic signal (i.e., turn-on signal). This signal signifies that injection control unit 50 is drawing less than 680 mA, and thus functioning in the idle mode of operation. Conversely, when the output voltage at its positive input is greater than 0.68V, the comparator chip outputs a high level logic signal (i.e., turn-off signal). This turn-off signal indicates that injection control unit 50 is drawing more than 680 mA, and thus functioning in the non-idle mode of operation.

The charging stage 440 features a charging circuit 450 and the activating transistor 470. The charging circuit 450 includes a battery charger controller 451, a pass transistor 455, a sense resistor $R_3$, a resistor divider network 460, and a Schottky diode 469. The battery charger controller 451 is preferably implemented as the Unitrode UC3906 controller chip produced by Texas Instruments Inc. and disclosed in Datasheet SLUS186B (Rev. July 2003), incorporated herein by reference. The activating transistor 470 is preferably the SFW/I9Z24 P-channel MOSFET made by Fairchild Semiconductor Corporation, and pass transistor 455 can take the form of a PNP transistor such as the KSE45H11 power transistor made by ST Microelectronics.

The activating transistor 470 is connected by its source to the 15V DC power supply 120 from which the charging circuit 450 receives its power. By its drain, transistor 470 connects to the $+V_{IN}$ and CURRENT SENSE+ terminals of chip 451 and, through sense resistor $R_3$, to the emitter or input of pass transistor 455. The collector or output of pass transistor 455 connects, via Schottky diode 469, to the $V_{Batt}$ terminal of batteries 143 and to the anodes of Schottky Barrier diodes 430. The drain of transistor 470 is also connected, via series diode 471 and Schottky diode 472, to the cathodes of Schottky Barrier diodes 430 and the $V_{IN+}$ input of current shunt monitor 421 as well as to sampling resistors $R_6$ and $R_7$. The sense resistor $R_3$ is connected across the $+V_{IN}$ and CURRENT SENSE+ terminals and the CURRENT LIMIT and CURRENT SENSE− terminals of chip 451. Resistors $R_4$, $R_8$, $R_9$ and $R_{10}$ of resistor divider network 460 are variously connected to the VOLTAGE SENSE, CHARGE ENABLE, STATE LEVEL CONTROL and POWER INDICATE terminals of chip 451. Resistor $R_5$ connects between the TRICKLE BIAS terminal of battery charger controller chip 451 and the collector (output) of pass transistor 455.

The PNP pass transistor 455 has its base connected to, and is thus controlled by, the DRIVER SINK terminal of battery charger controller 451. Similarly, the P-channel MOSFET activating transistor 470 has its gate connected to, and is thus controlled by, the output of differential comparator 425 (i.e., the output of output selector stage 410). When its gate receives the turn-off signal from output selector stage 410 (i.e., injection control unit 50 is operating in its non-idle mode), transistor 470 disconnects its source and drain terminals, thus effectively disconnecting power supply 120 from charging circuit 450 and injection control unit 50. In this state, when the activating transistor 470 is turned off, the Schottky Barrier diodes 430 are forward biased, thus leaving the batteries 143 to power the injection control unit. Conversely, when its gate receives the turn-on signal (i.e., injection control unit 50 is operating in its idle mode), transistor 470 turns on, thus connecting power supply 120 to the charging circuit 450 and the injection control unit 50. In this state, when the activating transistor 470 is turned on, the Schottky Barrier diodes 430 are obviously reversed biased.

In this context, the CBC system 100 has been designed to charge the batteries 143 of injection control unit 50 and thus enable the operator to use the injector system continuously without the burden of swapping batteries. The CBC system achieves these goals through two modes of charging: a low current charging mode and a multi-state charging mode. Whether disconnected from the injection control unit 50 or connected thereto while it operates in the idle mode, as long as battery pack 140 is connected to the power supply 120, the battery charger controller 451 will charge the batteries 143. The particular charging mode in which it operates depends on the voltage of batteries 143, as typically measured at the $V_{Batt}$ terminal. The charger controller 451 will enter neither mode until output selector stage 410 has output the turn-on signal to activating transistor 470, under the circumstances noted above, and the transistor 470 has responded thereto by connecting the power supply 120 to the charging circuit 450.

When the power supply 120 is disconnected from the battery pack 140, Schottky diode 469 prevents the batteries 143 from discharging through the charging circuit 450. For the preferred application of injection control unit 50, as shown in FIG. 6A, it is preferred that the resistor $R_{10}$ of resistor divider network 460 be connected to the POWER INDICATE terminal of chip 451 instead of ground. This will keep discharging in this circumstance to an absolute minimum.

With DC power supplied to charging circuit 450 via transistor 470, the CBC system 100 functions in the low current charging mode only when the voltage of the batteries 143 has dropped below a preselected minimum. More specifically, at its VOLTAGE SENSE terminal inter alia, the battery charger controller 451 monitors the voltage at the $V_{Batt}$ terminal via resistor divider network 460. As is apparent from FIG. 6A, the values of the resistors $R_4$, $R_8$, $R_9$ and $R_{10}$ determine the value of this preselected minimum. For the preferred application of injection control unit 50, the values of these resistors are preferably selected so that whenever $V_{Batt}$ drops below 10.8V the corresponding voltage at the VOLTAGE SENSE terminal will compel the chip 451 to enter its low current charging mode of operation. In this mode, the battery charger controller 451 does not activate (i.e., turns off) pass transistor 455 but instead supplies current from its TRICKLE BIAS terminal to the batteries 143 ($V_{Batt}$ terminal) via resistor $R_5$ and Schottky diode 469. The output current of the chip 451 is limited to this low or trickle level until the voltage of batteries 143 ($V_{Batt}$ terminal) reaches the preselected minimum level. Without this low current charging mode, the battery charger controller 451 would otherwise charge the batteries 143 at a high current even if a battery cell was shorted.

The battery charger controller 451 continues trickle charging the batteries 143 until they reach the preselected minimum of 10.8V, and in the process prevents high current charging if a battery cell is shorted. The controller chip 451 uses the 10.8V level as the minimum voltage required for the CBC system 100 to begin functioning in the multi-state charging mode.

Figure 7:
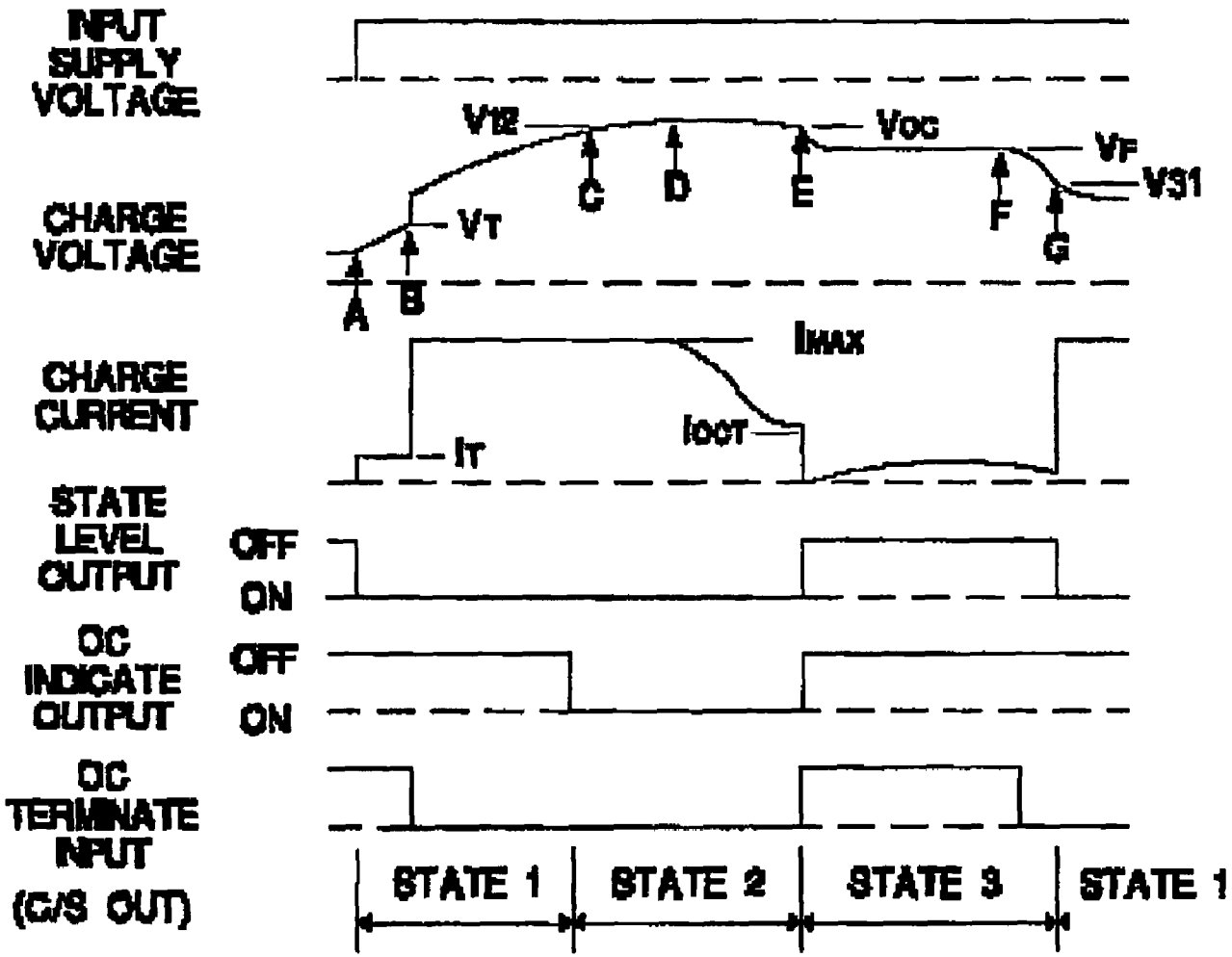
FIG. 7 is a graph showing the charging modes of the charging module according to the preferred embodiment of the invention.

The UC3906 controller chip 451 in its multi-state charging mode is capable of charging the batteries 143 according to three separate charge states: a high current bulk-charge state, a controlled over-charge state, and a precision float-charge or standby state. As shown in FIG. 7, the particular charge state in which chip 451 operates depends variously on the voltage of batteries 143 and the charging current supplied to the batteries via pass transistor 455, which chip 451 controls by controlling the bias applied to the base of the pass transistor 455.

With reference to FIG. 7, once the voltage of the batteries 143 reaches or exceeds the preselected minimum ($V_T$) of 10.8V, the battery charger controller 451 will begin charging the batteries 143 according to the bulk-charge state (STATE 1). In this state, the controller chip 451 will supply via pass transistor 455 a peak charge current ($I_{MAX}$) that is determined in part by sense resistor $R_3$, as disclosed in Datasheet SLUS186B (Rev. July 2003) cited above. For the preferred application of injection control unit 50, the value of sense resistor $R_3$ is preferably selected so that the peak charge current is on the order of 750 mA. The controller chip 451 continues charging the batteries 143 according to the bulk-charge state until the battery voltage ($V_{Batt}$) reaches a set percentage of an overcharge level ($V_{OC}$). For the preferred application of injection control unit 50, the set percentage and the overcharge level are preferably 95% and 14.7V, respectively. As with the preselected minimum voltage, these values are determined by the values of the resistors in resistor divider network 460. Once the battery voltage reaches or exceeds 95% of 14.7V (i.e., $V_{12}\approx 13.97V$), the charger controller 451 transitions to the over-charge state (STATE 2). In this state, chip 451 continues charging the batteries 143 until the charging current falls to a minimum threshold ($I_{OCT}\approx 75$ mA), which is determined by chip 451 and sense resistor $R_3$. When the charging current falls below the minimum threshold, the controller chip 451 transitions to the standby state (STATE 3). In this state, the chip applies to the batteries a constant voltage, which is determined by appropriate selection of the resistors in network 460. The charging stage 440 will remain in the standby state until the battery voltage drops a specified percentage below a float level ($V_F$) upon which the chip 451 will commence operating according to the bulk-charge state. For the preferred application of injection control unit 50, the specified percentage and the float level are preferably 10% and 13.5V, respectively. The bulk-charge state thus preferably restarts when the battery voltage drops to $V_{31}\approx 12.15V$. These values are also determined, at least in part, by resistors $R_4$, $R_8$, $R_9$ and $R_{10}$ of resistor divider network 460, as disclosed in Datasheet SLUS186B.

Referring to the alphabetic designations in FIG. 7, the controller chip 451 in its low current and multi-state charging modes operates as summarized below. At position A, the input power turns on, and the battery charges at the trickle current rate. At position B, the battery voltage $V_{Batt}$ reaches $V_T$. This enables the driver chip 451 and turns off its trickle bias output, and allows the battery to charge at the $I_{MAX}$ rate. At position C, the transition voltage $V_{12}$ is reached and the controller chip 451 now operates in the over-charge state. At position, D, the battery voltage approaches the over-charge level $V_{OC}$ and the charge current begins to taper. At position E, the charge current tapers to $I_{OCT}$. The CURRENT SENSE output (CSOUT), preferably tied to the OC TERM terminal, goes high. The controller chip 451 then changes to the float state and holds the battery voltage $V_{Batt}$ at $V_F$. At position F, the injection control unit 50 begins to discharge the battery 143 at a current greater than $I_{MAX}$. At position G, the load discharges the battery such that the battery voltage $V_{Batt}$ falls below $V_{31}$. The controller chip 451 then again operates in the bulk-charge state (STATE 1).

The indicator stage 480 includes a comparator circuit 481 and an indicator 482. The comparator circuit 481 can be implemented with the LM2903MX differential comparator chip produced by Fairchild Semiconductor Corporation. The indicator 482 can take the form of the KA-3528MBC surface mountable light-emitting diode (LED) chip produced by Kingbright Corporation. Differential comparator 481 has its positive input connected to the 5V DC received from regulator 490 and its negative input connected to a resistor divider network, $R_{15}$ and $R_{17}$. The output of comparator 481 is connected to the cathode of LED 482 via resistor $R_{14}$, with the anode of LED 482 connected to power supply 120.

The resistor divider network of $R_{15}$ and $R_{17}$ steps down the 15V DC received from power supply 120. For the preferred application of injection control unit 50, it is preferred that the values of resistors $R_{15}$ and $R_{17}$ be selected so that LED 482 will illuminate when the voltage from power supply 120 is greater than or equal to a preset upper level of 14.4V. This is because that, for the preferred application, 14.4V is the minimum voltage required to efficiently charge the batteries 143. Conversely, when the voltage from power supply 120 is less than a preset lower level of 13.8V, LED 482 will not illuminate. LED 482 may be on or off in the transition region between 13.8 V and 14.4 V. The purpose of indicator 482 is preferably to indicate to the operator that the power supply 120 is operational and is delivering the required minimum voltage to the battery pack 140.

Having now described in detail the preferred implementation of each stage of charger module 400, it should now be apparent that each stage could alternatively be fashioned from different circuit components or other arrangements of circuit components. Such different components or other arrangements of components that together perform the same function as any one of the cited stages are intended to be encompassed by the following claims.

Figure 8A:
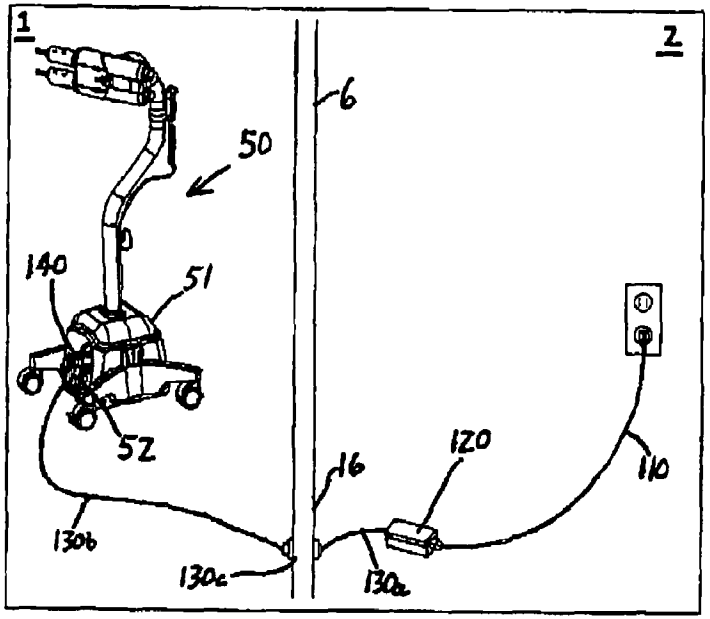
FIG. 8A illustrates a first configuration for the invention wherein the power supply and AC power cord are situated in the control room of the MR suite, and the DC power cord is routed through the penetration panel separating the control and scanner rooms and is connected to the battery pack of the invention in the scanner room.

The CBC system 100 can be deployed in any one of at least two configurations, namely, the scanner room configuration or the control room configuration. FIG. 8A shows the CBC system 100 deployed in the MR suite according to the control room configuration. In this configuration, the power supply 120 and its AC power cord 110 are situated in the control room 2 of the MR suite, with the AC power cord 110 plugged into an AC outlet. The DC power cord 130 from power supply 120 is routed through the penetration panel 16 separating the control and scanner rooms, and eventually connects to the battery pack 140 in the scanner room 1.

Figure 8B:
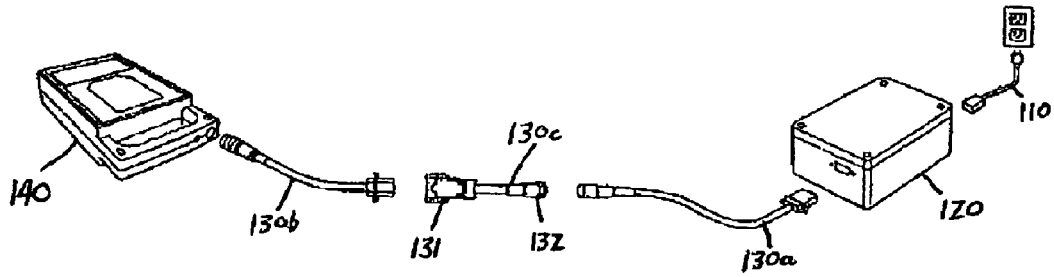
FIG. 8B shows a preferred manifestation of the DC power cord of FIG. 8A.
Figure 8C:
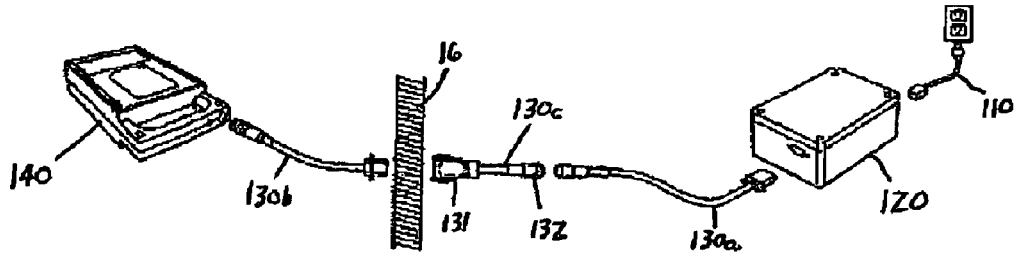
FIG. 8C illustrates one way of routing the DC power cord of FIG. 8B through the penetration panel.
Figure 8D:
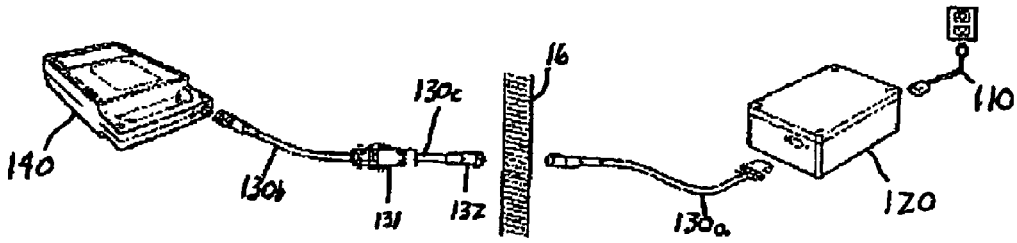
FIG. 8D illustrates another way of routing the DC power cord of FIG. 8B through the penetration panel.

FIG. 8B shows a preferred approach for routing the DC power cord 130 through the penetration panel 16. In this preferred manifestation, the DC power cord 130 includes a filtered cable section 130c routed into an aperture in penetration panel 16 and two shielded cable sections 130a and 130b connected thereto on opposite sides of the penetration panel 16. The filtered cable section 130c preferably comprises a D-shell connector 131 at one end and a circular connector 132 at the other end. As shown in FIG. 8C, if the penetration panel 16 has a 9-pin connector hole available as an aperture, then filtered cable section 130c can have its D-shell connector 131 inserted into the hole from the control room side and connected with its corresponding mate on shielded cable section 130b. Similarly, as shown in FIG. 8D, if the penetration panel 16 has a circular or similar hole available as an aperture, then filtered cable section 130c can have its circular connector 132 inserted into the hole from the scanner room side and connected with its corresponding mate on shielded cable section 130a. Ferrite clamps (not shown) are preferably installed on both ends of cable section 130b. The cable section 130a in the control room 2 connects the power supply 120 to the filtered cable section 130c, and cable section 130b in the scanner room 1 connects the filtered cable section 130c to battery pack 140. The battery pack 140 then plugs into the socket 52 of injection control unit 50.

Figure 9:
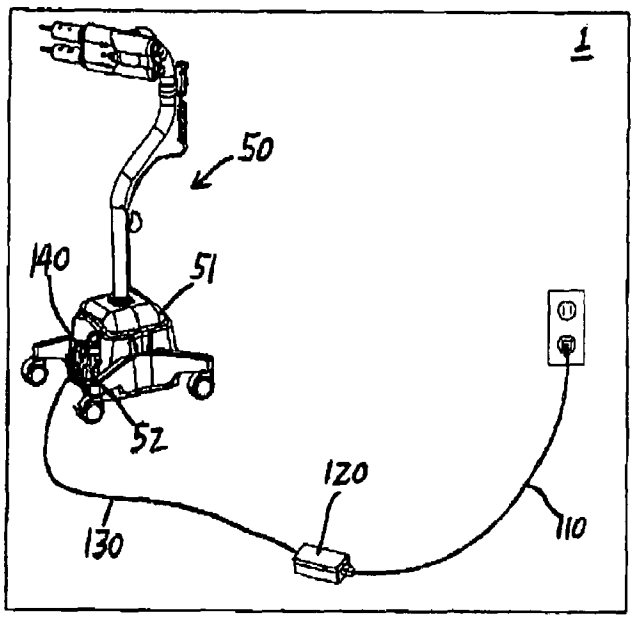
FIG. 9 illustrates a second configuration for the invention wherein the power supply, the battery pack, and the DC power cord interconnecting them are all situated within the scanner room of the MR suite, with the AC power cord from the power supply plugged into an AC outlet in the scanner room.

FIG. 9 shows the CBC system 100 deployed in the MR suite according to the scanner room configuration. In this configuration, the AC power cord 100, the power supply 120, the DC power cord 130 and the battery pack 140 are all situated in the scanner room 1 of the MR suite. The power supply 120 should be securely mounted to the floor or a wall at a sufficient distance from the scanner to avoid causing artifacts in the images. The AC power cord 110 is plugged into an AC outlet in the scanner room, preferably as far away as possible from the scanner. The DC power cord 130 interconnects the power supply 120 and the battery pack 140, with the battery pack 140 plugged into the socket 52 of injection control unit 50. In this configuration, both of the power cords 110 and 120 are preferably shielded.

Figure 10:
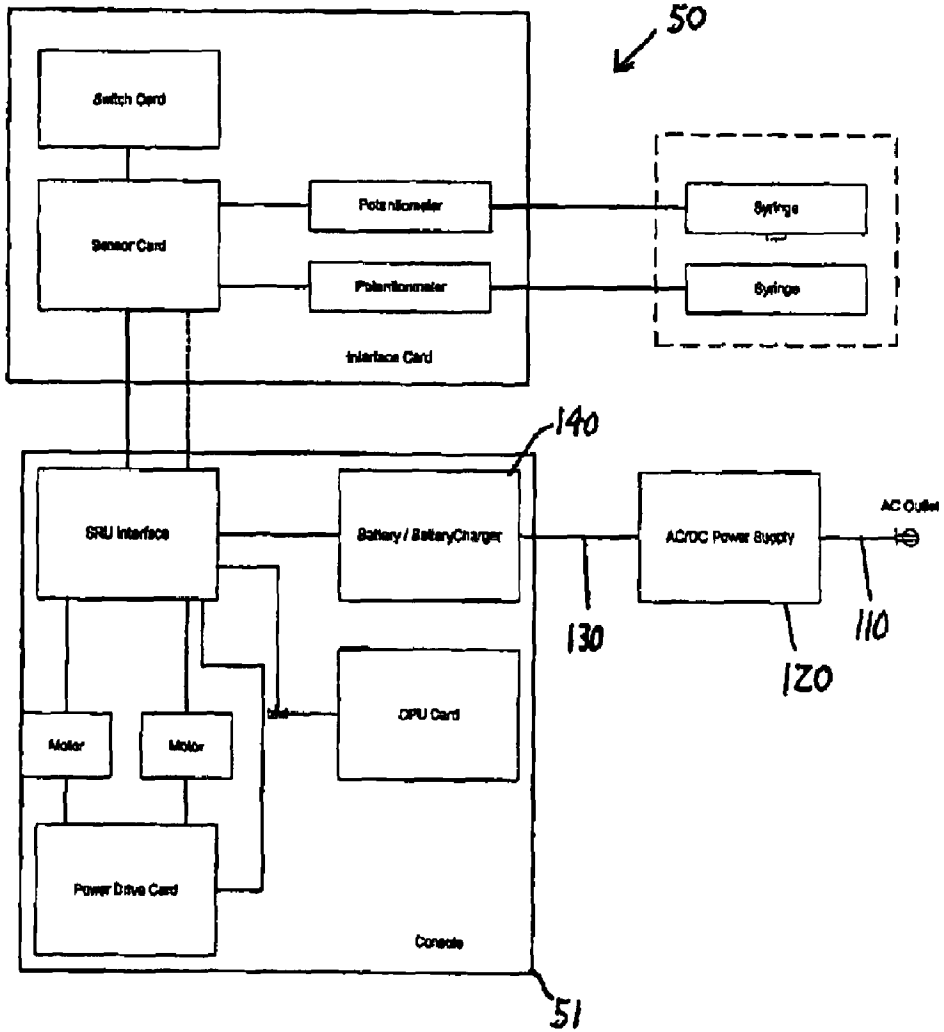
FIG. 10 illustrates a block diagram of the invention as used with an injector control unit.

The CBC system 100 and its preferred application of injection control unit 50, also referred to as a scanner room unit (SRU), are shown in FIG. 10 in block diagram form.

The presently preferred and alternative embodiments for carrying out the invention have been set forth in detail according to the Patent Act. Persons of ordinary skill in the art to which this invention pertains may nevertheless recognize alternative ways of practicing the invention without departing from the spirit of the following claims. Consequently, all changes and variations which fall within the literal meaning, and range of equivalency, of the claims are to be embraced within their scope. Persons of such skill will also recognize that the scope of the invention is indicated by the following claims rather than by any particular example or embodiment discussed or illustrated in the foregoing description.

Accordingly, to promote the progress of science and useful arts, we secure for ourselves by Letters Patent exclusive rights to all subject matter embraced by the following claims for the time prescribed by the Patent Act.

What is claimed is:

1. A battery charger system for an injector system, said injector system having an idle mode of operation and a non-idle mode of operation, the battery charger system comprising:

(a) a first power cord for conveying AC power from a source thereof;

(b) an AC/DC converter for converting the AC power received from said first power cord to DC power;

(c) a second power cord for conveying the DC power received from an output of said AC/DC converter; and (d) a battery pack including a battery and a charging module, said charging module for receiving the DC power from said AC/DC converter via said second power cord and for monitoring the operating mode of said injector system such that when said injector system is operating in (I) said idle mode, said charger module provides the DC power received from said AC/DC converter to said battery for the charging thereof and (II) said non-idle mode, said charger module prevents the DC power from said AC/DC converter from reaching said battery and thus enables said battery to provide DC power to said injector system.

2. The battery charger system of claim 1 wherein said charger module also provides the DC power received from said AC/DC converter to said injector system when said injector system is operating is said idle mode of operation.

3. The battery charger system of claim 1 wherein said charger module also enables the DC power from said AC/DC converter to charge said battery when said battery pack is disconnected from said injector system.

4. The battery charger system of claim 1 wherein, when said AC/DC converter is disconnected from said battery pack, said charging module enables said battery to provide DC power to said injector system whether said injector system is operating in said non-idle mode or said idle mode.

5. The battery charger system of claim 1 wherein said second power cord comprises:

(a) a central section for routing into an aperture of a penetration panel;

(b) a first end section on a first side of the penetration panel for interconnecting said central section and said AC/DC converter; and (c) a second end section on a second side of the penetration panel for interconnecting said central section and said battery pack.

6. The battery charger system of claim 5 wherein said central section comprises:

(a) a circular connector at one end thereof for connection to said first end section; and (b) a D-shell connector at another end thereof routed into said aperture for connection to said second end section.

7. The battery charger system of claim 5 wherein said central section comprises:

(a) a D-shell connector at one end thereof for connection to said second end section; and (b) a circular connector at another end thereof routed into said aperture for connection to said first end section.

8. The battery charger system of claim 5 further comprising ferrite clamps installed on both ends of said second end section.

9. A battery charger system for use with an injection control unit of an injector system, the battery charger system comprising:

(a) an AC/DC converter for converting AC power from a source thereof to DC power; and (b) a battery pack including a battery and a charging module, said charging module for monitoring an operating mode of said injector system such that when said battery pack is:

(I) disconnected from said injection control unit, said charging module enables said AC/DC converter to charge said battery with the DC power therefrom; and (II) connected to said injection control unit, (A) upon detecting said injector system in an idle mode of operation, said charger module routes the DC power from said AC/DC converter to both said battery for the charging thereof and said injection control unit for operation thereof; and (B) upon detecting said injector system in a non-idle mode of operation, said charger module prevents said AC/DC converter from charging said battery and enables said battery to provide DC power to said injection control unit.

10. The battery charger system of claim 9 wherein, when said AC/DC converter is disconnected from said battery pack, said charging module enables said battery to provide DC power to said injection control unit whether said injector system is operating in said non-idle mode or said idle mode.

11. The battery charger system of claim 9 further including a DC power cord for interconnecting said AC/DC converter and said battery pack on opposites sides of a penetration panel, said DC power cord comprising:

(a) a central section for routing into an aperture of the penetration panel;

(b) a first end section on a first side of the penetration panel for interconnecting said central section and said AC/DC converter; and (c) a second end section on a second side of the penetration panel for interconnecting said central section and said battery pack.

12. The battery charger system of claim 11 wherein said central section comprises:

(a) a circular connector at one end thereof for connection to said first end section; and (b) a D-shell connector at another end thereof routed into said aperture for connection to said second end section.

13. The battery charger system of claim 11 wherein said central section comprises:

(a) a D-shell connector at one end thereof for connection to said second end section; and (b) a circular connector at another end thereof routed into said aperture for connection to said first end section.

14. The battery charger system of claim 11 further comprising ferrite clamps installed on both ends of said second end section.

15. A battery charger system for use with a battery-powered system, the battery charger system comprising:

[(a) a power supply for supplying DC power; and]

[(b)] (*a*) a battery pack including a battery [and a charging module, said charging module connectible to], *said battery pack adapted for plugging into* said *battery-powered system and being connectible to a* power supply for receiving the DC power therefrom*;* and

[capable of] (*b*) *a charging module for* monitoring an operating mode of said battery-powered system [when linked thereto] such that when said battery pack is:

(I) disconnected from said battery-powered system, said [charging module enables] *battery is capable of being charged by* said power supply [to charge said battery] with the DC power *received* therefrom *when said power supply is connected to said battery pack*; and (II) [connected to] *plugged into* said battery-powered system, (A) upon detecting said battery-powered system in an idle mode of operation, said charger module routes the DC power from said power supply to both said battery for the charging thereof and said battery-powered system for operation thereof; and (B) upon detecting said battery-powered system in a non-idle mode of operation, said charger module prevents said power supply from charging said battery and enables said battery to provide DC power to said battery-powered system*;*

*wherein said charging module includes an output selector stage and a charging stage such that:*

(*III*) *said output selector stage senses current drawn by said battery-powered system and provides a turn-on signal when said current is less than a predetermined level and a turn-off signal when said current is greater than said predetermined level; and*

(*IV*) *said charging stage is connected to said output selector stage such that upon receiving* (*A*) *said turn-off signal, said charging stage prevents said battery from being charged by said power supply and enables said battery to provide DC power to said battery-powered system and* (*B*) *said turn-on signal, said charging stage enables DC power from said power supply to be conveyed to said battery-powered system and assumes:*

(*i*) *a low current charging mode, when a voltage level of said battery is less than a preselected minimum level, wherein said charging stage charges said battery with a charging current therefor limited to a trickle level, and*

(*ii*) *a multi-state charging mode, when said voltage level of said battery is said preselected minimum level or greater, wherein said charging stage operates according to:* (*a*) *a bulk-charge state, when said voltage level of said battery is said preselected minimum level or greater yet below a set percentage of an overcharge level, wherein said charging stage charges said battery with said charging current at a peak level thereof,* (*b*) *an over-charge state, when said voltage level of said battery is*

*equal to or exceeds said set percentage of said overcharge level, wherein said charging stage continues charging said battery until said charging current falls to a minimum threshold, and (c) a standby state, when said charging current falls below said minimum threshold, wherein said charging stage applies a constant voltage to said battery until said voltage level of said battery drops at least a specified percentage below a float level upon which said charging stage will commence operating according to said bulk-charge state.*

16. The battery charger system of claim 15 wherein, when *said battery pack is connected to said battery-powered system and* said power supply is disconnected from said battery pack, said charging module enables said battery to provide DC power to said battery-powered system whether said battery-powered system is operating in said non-idle mode or said idle mode.

17. The battery charger system of claim 15 wherein said battery-powered system is an injector system.

18. The battery charger system of claim 15 further including a DC power cord for interconnecting said power supply and said battery pack on opposite sides of a barrier, said DC power cord comprising:

(a) a central section for routing into an aperture of the barrier;

(b) a first end section on a first side of the barrier for interconnecting said central section and said power supply; and (c) a second end section on a second side of the barrier for interconnecting said central section and said battery pack.

19. The battery charger system of claim 18 wherein said central section comprises:

(a) a circular connector at one end thereof for connection to said first end section; and (b) a D-shell connector at another end thereof routed into said aperture for connection to said second end section.

20. The battery charger system of claim 18 wherein said central section comprises:

(a) a D-shell connector at one end thereof for connection to said second end section; and (b) a circular connector at another end thereof routed into said aperture for connection to said first end section.

21. The battery charger system of claim 18 further comprising ferrite clamps installed on both ends of said second end section.

22. A charging module for a battery for use with an injection control unit of an injector system, the charging module comprising:

(a) an output selector stage for sensing a mode of operation of said injection control unit and for providing a turn-on signal when said injection control unit is operating in an idle mode and a turn-off signal when said injection control unit is operating in a non-idle mode;

(b) a charging stage connected to said output selector stage such that upon receiving (I) said turn-off signal, said charging stage prevents said battery from being charged by a power supply therefor and enables said battery to provide DC power to said injection control unit and (II) said turn-on signal, said charging stage enables DC power from said power supply to be conveyed to said injection control unit and assumes:

(A) a low current charging mode, when a voltage level of said battery is less than a preselected minimum level, wherein said charging stage charges said battery with a charging current therefor limited to a trickle level, and (B) a multi-state charging mode, when said voltage level of said battery is said preselected minimum level or greater, wherein said charging stage operates according to:

(i) a bulk-charge state, when said voltage level of said battery is said preselected minimum level or greater yet below a set percentage of an over-charge level, wherein said charging stage charges said battery with said charging current at a peak level thereof, (ii) an over-charge state, when said voltage level of said battery is equal to or exceeds said set percentage of said overcharge level, wherein said charging stage continues charging said battery until said charging current falls to a minimum threshold, and (iii) a standby state, when said charging current falls below said minimum threshold, wherein said charging stage applies a constant voltage to said battery until said voltage level of said battery drops at least a specified percentage below a float level upon which said charging stage will commence operating according to said bulk-charge state; and (c) an indicator stage for indicating when said power supply is capable of providing to the charging module sufficient power to efficiently charge said battery.

23. The charging module of claim 22 wherein said output selector stage includes:

(a) a current monitoring circuit for sensing current drawn by said injection control unit and for outputting an output voltage (I) less than a predetermined threshold when said current is less than a predetermined level thereby indicating that said injection control unit is operating in said idle mode and (II) greater than said predetermined threshold when said current is greater than said predetermined level thereby indicating that said injection control unit is operating in said non-idle mode; and (b) a comparator circuit for comparing said output voltage of said current monitoring circuit with a nominal reference voltage such that when said output voltage is (I) less than said predetermined threshold, said comparator circuit outputs said turn-on signal and (II) greater than said predetermined threshold, said comparator circuit outputs said turn-off signal.

24. The charging module of claim 23 wherein said current monitoring circuit includes:

(a) a current shunt monitor for monitoring said current drawn by said injection control unit and outputting an interim current proportional thereto; and (b) an external load resistor for converting said interim current into said output voltage corresponding thereto.

25. The charging module of claim 22 wherein said charging stage includes an activating transistor and a charging circuit such that:

(a) said activating transistor is connected to said output selector stage so that upon receiving (I) said turn-on signal, said activating transistor operably connects said power supply to said charging circuit and (II) said turn-off signal, said activating transistor operably disconnects said power supply from said charging circuit; and (b) said charging circuit is responsive to (I) said turn-off signal by preventing said battery from being charged by said power supply and enabling said battery to provide DC power to said injection control unit and (II) said turn-on signal by being operable variously in said low current charging mode and said multi-state charging mode depending on said voltage level of said battery.

26. The charging module of claim 25 wherein said charging circuit includes a Unitrode UC3906 battery charger controller chip.

27. The charging module of claim 25 wherein said activating transistor is a P-channel MOSFET.

28. The charging module of claim 25 wherein said indicator stage includes:

(a) a light-emitting diode having an anode connected to said power supply; and (b) a comparator circuit having an output connected to a cathode of said light-emitting diode, said comparator circuit for comparing an output voltage of said power supply with a reference voltage such that when said output voltage is (I) greater than a preset upper level, said comparator circuit turns on said light-emitting diode and (II) less than a preset lower level, said comparator circuit turns off said light-emitting diode.

29. A charging module for a battery for use with a battery-powered system, the charging module comprising:

(a) an output selector stage for sensing current drawn by said battery-powered system and for providing a turn-on signal when said current is less than a predetermined level and a turn-off signal when said current is greater than said predetermined level; and (b) a charging stage connected to said output selector stage such that upon receiving (I) said turn-off signal, said charging stage prevents said battery from being charged by a power supply therefor and enables said battery to provide DC power to said battery-powered system and (II) said turn-on signal, said charging stage enables DC power from said power supply to be conveyed to said battery-powered system and assumes:

(A) a low current charging mode, when a voltage level of said battery is less than a preselected minimum level, wherein said charging stage charges said battery with a charging current therefor limited to a trickle level, and (B) a multi-state charging mode, when said voltage level of said battery is said preselected minimum level or greater, wherein said charging stage operates according to:

(i) a bulk-charge state, when said voltage level of said battery is said preselected minimum level or greater yet below a set percentage of an over-charge level, wherein said charging stage charges said battery with said charging current at a peak level thereof, (ii) an over-charge state, when said voltage level of said battery is equal to or exceeds said set percentage of said overcharge level, wherein said charging stage continues charging said battery until said charging current falls to a minimum threshold, and (iii) a standby state, when said charging current falls below said minimum threshold, wherein said charging stage applies a constant voltage to said battery until said voltage level of said battery drops at least a specified percentage below a float level upon which said charging stage will commence operating according to said bulk-charge state.

30. The charging module of claim 29 further comprising an indicator stage for indicating when said power supply is capable of providing to the charging module sufficient power to efficiently charge said battery.

* * * * *